US009605030B2

(12) United States Patent
Yuste Herranz et al.

(10) Patent No.: US 9,605,030 B2
(45) Date of Patent: Mar. 28, 2017

(54) RAPID SELECTION METHOD FOR HIV GP-120 VARIANTS

(75) Inventors: María Eloísa Yuste Herranz, Barcelona (ES); Víctor Sánchez Merino, Barcelona (ES); Carolina Ferreira, Barcelona (ES)

(73) Assignees: LABORATORIOS DEL DR. ESTEVE, S.A., Barcelona (ES); FUNDACIÓ PRIVADA INSTITUT DE RECERCA DE LA SIDA-CAIXA, Badalona (ES)

( * ) Notice: Subject to any disclaimer, the term of this patent is extended or adjusted under 35 U.S.C. 154(b) by 220 days.

(21) Appl. No.: 14/000,924

(22) PCT Filed: Feb. 24, 2012

(86) PCT No.: PCT/EP2012/053185

§ 371 (c)(1),
(2), (4) Date: Oct. 16, 2013

(87) PCT Pub. No.: WO2012/113921

PCT Pub. Date: Aug. 30, 2012

(65) Prior Publication Data

US 2014/0037667 A1 Feb. 6, 2014

Related U.S. Application Data

(60) Provisional application No. 61/446,595, filed on Feb. 25, 2011.

(30) Foreign Application Priority Data

Feb. 25, 2011 (EP) .................................... 11382051

(51) Int. Cl.

| | |
|---|---|
| ***C07K 14/16*** | (2006.01) |
| ***G01N 33/68*** | (2006.01) |
| ***C07K 14/005*** | (2006.01) |
| ***C12N 15/10*** | (2006.01) |
| ***C07K 16/10*** | (2006.01) |
| ***G01N 33/569*** | (2006.01) |
| *A61K 39/00* | (2006.01) |

(52) U.S. Cl.

CPC ........ *C07K 14/005* (2013.01); *C07K 16/1063* (2013.01); *C12N 15/1037* (2013.01); *G01N 33/56988* (2013.01); *G01N 33/6854* (2013.01); *A61K 39/00* (2013.01); *C07K 2317/76* (2013.01); *C12N 2740/16043* (2013.01); *C12N 2740/16122* (2013.01); *C12N 2799/027* (2013.01); *G01N 2333/162* (2013.01); *G01N 2469/20* (2013.01)

(58) Field of Classification Search

CPC ........... C07K 16/1063; C07K 16/2812; C07K 14/7051; C07K 14/005; C07K 2319/00; A61K 38/00; A61K 39/21; C12N 2740/16134; C12N 2740/16222; C12N 2740/16234; C12N 2740/16322; G01N 33/56988

See application file for complete search history.

(56) References Cited

U.S. PATENT DOCUMENTS

| | | | | |
|---|---|---|---|---|
| 5,753,503 | A | 5/1998 | Katinger et al. | |
| 5,817,316 | A * | 10/1998 | Sodroski | C07K 16/1063 424/184.1 |
| 5,858,366 | A * | 1/1999 | Sodroski | C07K 16/1063 424/184.1 |
| 5,911,989 | A | 6/1999 | Katinger et al. | |
| 7,470,430 | B2 * | 12/2008 | Nabel | A61K 39/12 424/208.1 |
| 8,071,107 | B2 * | 12/2011 | Haynes | A61K 39/21 424/208.1 |
| 8,586,056 | B2 * | 11/2013 | Phogat | C07K 14/005 424/186.1 |
| 9,051,362 | B2 | 6/2015 | Chan-Hui et al. | |
| 2004/0033487 | A1 * | 2/2004 | Nabel | A61K 39/12 435/5 |
| 2007/0178562 | A1 * | 8/2007 | Haynes | A61K 39/21 435/91.1 |

(Continued)

FOREIGN PATENT DOCUMENTS

| | | |
|---|---|---|
| CN | 1339319 | 3/2002 |
| WO | WO 9104273 | 4/1991 |

(Continued)

OTHER PUBLICATIONS

Bontjer et al. Optimization of Human Immunodeficiency Virus Type 1 Envelope Glycoproteins with V1/V2 Deleted Using Virus Evolution. Journal of Virology, Jan. 2009, vol. 83, No. 1, p. 368-383.*
Starcich et al. Cell, 1986, vol. 45, pp. 637-648.*
O'Brien et al. Nature vol. 348, pp. 63-73.*
Wu et al. J. Virol. 2006, vol. 80, No. 22, pp. 11393-11397.*
Pantophlet et al. Annual Review of immunology, 2006, vol. 24, pp. 739-769.*
Koff et al. Vaccine 2013, vol. 31, Supplement 2, pp. B204-B208.*
Li et al. Journal of Virology, 2005, vol. 79 (16), pp. 10108-10125).*

(Continued)

*Primary Examiner* — Bao Li
(74) *Attorney, Agent, or Firm* — Jenkins, Wilson, Taylor & Hunt, P.A.

(57) ABSTRACT

The invention relates to a method for rapid immunogen selection (RIS) based on the binding a library of recombinant viruses containing randomized HIV gp120 variants of a surface polypeptide displayed to said neutralizing antibodies. The invention relates as well to the use of the HIV gp120 immunogens isolated according to the RIS method of the invention in medicine for the treatment of diseases caused by a virus and in diagnosis for the identification of neutralizing antibodies in a patient.

9 Claims, 6 Drawing Sheets

(56) References Cited

U.S. PATENT DOCUMENTS

2011/0262488 A1* 10/2011 Phogat ................. C07K 14/005
424/400
2014/0037667 A1 2/2014 Yuste Herranz et al.

FOREIGN PATENT DOCUMENTS

| | | | |
|---|---|---|---|
| WO | WO 9407922 | | 4/1994 |
| WO | WO 9633219 | | 10/1996 |
| WO | WO 01/98514 A2 | | 12/2001 |
| WO | WO2005028625 | * | 3/2005 |
| WO | WO 2010107939 | | 9/2010 |

OTHER PUBLICATIONS

Kwong et al., "Structure of an HIV gp120 envelope glycoprotein in complex with the CD4 receptor and a neutralizing human antibody," Nature. vol. 393, pp. 648-659 (1998).
Moore et al., "Probing the structure of the human immunodeficiency virus surface glycoprotein gp120 with a panel of monoclonal antibodies," Journal of Virology. vol. 68, No. 1 pp. 469-484 (1994).
Moore et al., "Antibody cross-competition analysis of the human immunodeficiency virus type 1 gp120 exterior envelope glycoprotein," Journal of Virology. vol. 70, No. 3 pp. 1863-1872 (1996).
Parren et al., "The neutralizing antibody response to HIV-1: viral evasion and escape from humoral immunity," AIDS. vol. 13, Supp. A pp. S137-S162 (1999).
Burton, "Antibodies, viruses and vaccines," Nature Reviews Immunology. vol. 2, pp. 706-713 (2002).
Zinkernagel et al., "Neutralizing antiviral antibody responses," Advances in Immunology. vol. 79, pp. 1-53 (2001).
McMichael et al., "HIV vaccines 1983-2003," Nature Medicine. vol. 9, No. 7 pp. 874-880 (2003).
McCutchan et al., "Subtype G and multiple forms of A/G intersubtype recombinant human immunodeficiency virus type 1 in Nigeria," Virology. vol. 254, pp. 226-234, (1999).
Shankarappa et al., "Consistent viral evolutionary changes associated with the progression of human immunodeficiency virus type 1 infection," Journal of Virology. vol. 73, No. 12 pp. 10489-10502 (1999).
Heyndrickx et al., "Simplified strategy for detection of recombinant human immunodeficiency virus type 1 group M isolates by *gag/env* heteroduplex mobility assay," Journal of Virology. vol. 74, No. 1 pp. 363-370 (2000).
McCutchan, "Understanding the genetic diversity of HIV-1," AIDS. vol. 14, Supp. 3 pp. S31-S44 (2000).
Robertson et al., "HIV-1 nomenclature proposal," Science. vol. 288, pp. 55-57 (2000).
Kuiken et al., "Evidence for limited within-person evolution of the V3 domain of the HIV-1 envelope in the Amsterdam population," AIDS. vol. 10, pp. 31-37 (1996).
Schilling et al., "Generation of a HI-viral packaging cell line as scaffolding for a lentiviral display system," Retrovirology. vol. 6, Supp. 3 p. 77 (2009).
Wagner, "Immunogen design and gene delivery," University of Regensburg (2006).
Bhattacharyya et al., "Design of a non-glycosylated outer domain-derived HIV-1 gp120 immunogen that binds to CD4 and induces neutralizing antibodies," Journal of Biological Chemistry. vol. 285, No. 35 pp. 27100-27110 (2010).
Li et al., "Human immunodeficiency virus type 1 env clones from acute and early subtype B infections for standardized assessments of vaccine-elicited neutralizing antibodies," Journal of Virology. vol. 79, No. 16 pp. 10108-10125 (2005).
Sa-Filho et al., "Characterization of the full-length human immunodeficiency virus-1 genome from recently infected subjects in Brazil," AIDS Research and Human Retroviruses. vol. 23, No. 9 pp. 1087-1094 (2007).
GenBank Accession No. EF637050.
Levin et al., "Optimizing the affinity and specificity of proteins with molecular display," Molecular BioSystems. vol. 2, pp. 49-57 (2006).
Urban et al., "Retroviral display in gene therapy, protein engineering, and vaccine development," ACS Chemical Biology. vol. 6, No. 1 pp. 61-74 (2010).
Taube et al., "Lentivirus display: stable expression of human antibodies on the surface of human cells and virus particles," PLoS One. vol. 3, No. 9 p. E3181 (2008).
Burton et al., "HIV vaccine design and the neutralizing antibody problem," Nature Immunology. vol. 5, No. 3 pp. 233-236 (2004).
European Search Report corresponding to European Application No. 11382051 dated Jul. 25, 2011.
International Search Report corresponding to International Application No. PCT/EP2012/053185 dated May 30, 2012.
Burton D, et al., Science 1994; 266: 1024-1027.
Cardoso R, et al., Immunity 2005; 22:163-173.
Ofek G, et al., J. Virol. 2004; 78:10724-10737.
Trkola A, et al., J. Virol. 1996; 70:1100-1108.
Wu X et al. Rational Design of Envelope Indentifies Broadly Neutralizing Human Monoclonal Antibodies to HIV-1. Science. Aug. 13, 2010; 329(5993): 856-861.

* cited by examiner

```
                                      130       140       150        16
                            ....|....| ....|....| ....|....| ....|....|
ENV AC10 SECUENCIADO        KLTPLCVTLS CTDNVGNDTS TNNSRWDKME KGEIKNCSFN
L1-1 CONTIG ENV             .......... .......... .......... .......Y..
L1-2 CONTIG ENV             ...Q..D... .......... .......... ..........
L1-3 CONTIG ENV             .......... ....E..... .........G ..........
L1-4 CONTIG ENV             .......... .......... ........I. ..........
L1-5 CONTIG ENV             .......... .......... .......... ..........
L1-6 CONTIG ENV             .......... .......... ........X. ..........
L2-1 CONTIG ENV             .......... .......... .......... ..........
L2-2 CONTIG ENV             .......... .......... .......... ....X.....
L2-3 CONTIG ENV             .......... ........I. .I........ ........C.
L2-4 CONTIG ENV             .......... .......... .......... ..........
L2-5 CONTIG ENV             .......... .......... .......... ..........
L3-2 contig env             .......... .......... .......... ..........
L3-3 CONTIG ENV             .......... .......... .......... ..........
L3-4 CONTIG ENV             .......... ....M..... .......... ..........
L3-5 CONTIG ENV             .......... .......... .......... ..........
Contig BR1 CLON1 pcDNA      .......... YN........ .......... ..........
Contig BR1 CLON2 pcDNA      .......... YN........ .......... ..........
Contig BR1 CLON3 pcDNA      .......... YK........ .......... ..........
Contig BR1 CLON4 pcDNA      .......... YK........ .......... ..........
Contig BR1 CLON 1           .......... YN.....G.. .......... .........Y
ContiG BR1 CLON 4           .......... YN.....G.. .......... .........Y
Contig BR1 CLON 6           .......... YN.....G.. .......... .........Y
```

```
SEQUENCED ENV AC10   MRVRETRKNY QHLWWKWGMM LLGMLMICSA VEQTWVTVYY GVPVWKEANT ILFCASDAKA YNTEVHNVWA THACVPTDPN
PG16 CLONE 10        .......... .......... .......... .......... .......... .......... .......... ..........

                             90        100        110        120        130        140        150        160
                     ....|....| ....|....| ....|....| ....|....| ....|....| ....|....| ....|....| ....|....|
SEQUENCED ENV AC10   PQEVELENVT ENFNMWKNNM VDQMHGDIIS LWDQSLKPCV KLTPLCVTLS CTDNVGNDTS TNNSRWDKME KGEIKNCSFN
PG16 CLONE 10        .......... .......... .......... .......... .......... .......... .......... ..........

                            170        180        190        200        210        220        230        240
                     ....|....| ....|....| ....|....| ....|....| ....|....| ....|....| ....|....| ....|....|
SEQUENCED ENV AC10   ITTNMRDKMQ KQYALFYKLD VVPIEEGKNN NSSFTDYRLI SCNTSVITQA CPKVTFEPIP IHYCAPAGFA LLKCKDKKFN
PG16 CLONE 10        .......... .......... .......... .......... ..S....... .......... .......... ..........

                            250        260        270        280        290        300        310        320
                     ....|....| ....|....| ....|....| ....|....| ....|....| ....|....| ....|....| ....|....|
SEQUENCED ENV AC10   GTGPCKNVST VQCTHGIKPV VSTQLLLNGS LAEEEVVIRS ENFSNNARTI IVQLNTSVEI KCIRPNNNTR KGIHIGPGRA
PG16 CLONE 10        .......... .......... .......... .......... .......... .......... .......... ..........

                            330        340        350        360        370        380        390        400
                     ....|....| ....|....| ....|....| ....|....| ....|....| ....|....| ....|....| ....|....|
SEQUENCED ENV AC10   FYTTGDIIGD IRQAHCNISR QNWNNTLKQI AEKLREQFGN KTIVFRNSSG GDPEIVMHTF NCAGEFFYCN TAELFNSTWY
PG16 CLONE 10        .......... .......... .......... .......... .......... .......... .......... ..........

                            410        420        430        440        450        460        470        480
                     ....|....| ....|....| ....|....| ....|....| ....|....| ....|....| ....|....| ....|....|
SEQUENCED ENV AC10   ANGTISIGGG NKTNIILPCR IKQFINMWQE VGKAMYAPPI SGQIRCSSNI TGLLLTRDGG RGNQTDNQTE IFRPVGGDMK
PG16 CLONE 10        .......... .......... .......... .......... .......... .......... .......... ..........

                            490        500        510        520        530        540        550        560
                     ....|....| ....|....| ....|....| ....|....| ....|....| ....|....| ....|....| ....|....|
SEQUENCED ENV AC10   NNWRSELYKY KVVRIEPLGI APTRAKRRVV QREKRAVGIG ALFLGFLGAA GSTMGAASMT LTVQARLLLS GIVQQQNNLL
PG16 CLONE 10        .......... .......... .......... .......... .......... .......... .......... ..........

                            570        580        590        600        610        620        630        640
                     ....|....| ....|....| ....|....| ....|....| ....|....| ....|....| ....|....| ....|....|
SEQUENCED ENV AC10   RAIEAQQHLL QLTVWGIKQL QARVLAVERY LRDQQLLGIW GCSGKLICTT AVPWNVSWNN RSVDDIWENM TWMQWDREIS
PG16 CLONE 10        .......... .......... .......... .......... ...E...... .......... .......... ..........

                            650        660        670        680        690        700        710        720
                     ....|....| ....|....| ....|....| ....|....| ....|....| ....|....| ....|....| ....|....|
SEQUENCED ENV AC10   NYTSLIYTLI EESQNQQEKN EQELLALDKW ANLWNWFNIT EWLWYIKIFI MIVGGLVGLR IVFAVLSIVN RVRQGYSPLS
PG16 CLONE 10        .......... .......... .......... .......... .......... .......... .......... ..........
```

FIG. 5

```
                                730        740        750        760        770        780        790        800
                         ....|....| ....|....| ....|....| ....|....| ....|....| ....|....| ....|....| ....|....|
SEQUENCED ENV AC10       FQTHLPAQRG PDRPGGIEEE GGESDRDRSG RLVNGFLAII WIDLRSLCLF SYHHLRDLLL IVTRIVEILG RRGWEILKYW
PG16 CLONE 10            .......... .......... .......... .......... .......... .......... .......... ..........

                                810        820        830        840        850        860
                         ....|....| ....|....| ....|....| ....|....| ....|....| ....|....| .
SEQUENCED ENV AC10       WNLLQYWIQE LKNSAVSLLN AIAIAVGEGT DRIIEAFRSI FRAILHIPTR IRQGLERSLL *
PG16 CLONE 10            .......... .......... .......... .......... .......... .......... *
```

FIG. 5 (cont.)

SEQUENCE LISTING

<160> NUMBER OF SEQ ID NOS: 32

<210> SEQ ID NO 1
<211> LENGTH: 2583
<212> TYPE: DNA
<213> ORGANISM: Artificial Sequence
<220> FEATURE:
<223> OTHER INFORMATION: Artificially synthesized env gene of the HIV AC10 isolate

<400> SEQUENCE: 1

```
atgagagtga gggagaccag gaagaattat cagcacttgt ggtggaaatg gggcatgatg     60
ctccttggga tgttgatgat ctgtagtgct gtagaacaaa cgtgggtcac agtctattat    120
ggggtacctg tgtggaaaga agcaaacacc attttatttt gtgcatcaga tgctaaagca    180
tataatacag aggtacataa tgtttgggcc acacatgcct gtgtacccac agaccccaac    240
ccacaagaag tagaattgga aaatgtgaca gaaaatttta acatgtggaa aaacaacatg    300
gtagatcaga tgcatgggga tataatcagt ttatgggatc aaagcctaaa gccatgtgta    360
aaattaactc cactctgtgt tactttaagt tgcactgata atgtgggaaa tgatactagt    420
accaataata gtagatggga taaaatggaa aaaggagaaa taaagaactg ctctttcaat    480
atcaccacaa acatgagaga taagatgcag aaacaatatg cactttttta taaacttgat    540
gtagtaccaa tagaggaagg taagaataat aacagtagtt ttaccgacta taggttgata    600
agttgtaaca cctcagtcat tacacaggcc tgtccaaagg taacctttga gccaattccc    660
atacattatt gtgccccagc tggttttgcg cttctaaaat gtaaggataa gaaattcaat    720
ggaacaggac catgtaaaaa tgttagcaca gtacaatgta cacatggaat taagccagta    780
gtatcaactc agctgctatt aaatggcagt ctagcagaag aagaggtagt aataagatct    840
gagaacttct cgaacaatgc tagaaccata atagtacagc tgaatacatc tgtagaaata    900
aagtgtataa gacccaacaa caatacaaga aaaggtatac atataggacc agggagagca    960
ttttatacaa caggagatat aataggagat ataagacaag cacattgtaa cattagtaga   1020
caaaattgga ataacacttt aaaacagata gctgaaaagt taagagaaca atttgggaat   1080
aaaacaatag tctttagaaa ctcctctgga ggggatccag aaattgtaat gcacactttt   1140
aattgtgcag gggaattttt ctactgtaat acagcagaac tgtttaatag tacttggtat   1200
gcaaatggca caattagtat tggagggggga aacaagacta atatcatact cccatgcaga   1260
ataaaacaat ttataaacat gtggcaggaa gtaggaaaag caatgtatgc ccctcccatc   1320
agtggacaga ttagatgttc atcaaatatt acaggactgc tattaacaag agatggtggt   1380
aggggcaatc agaccgacaa ccagactgag atcttcagac ctgtaggagg agatatgaaa   1440
aacaattgga gaagtgaatt atataaatat aaagtagtaa gaattgaacc attaggaata   1500
gcacccacca gggcaaaaag gagagtggtg cagagagaaa aaagagcagt gggaatagga   1560
gctttgttcc ttgggttctt gggagcagca ggaagcacta tgggcgcagc gtcaatgacg   1620
ctgacggtac aggccagact attattgtct ggtatagtgc aacagcagaa caatctgctg   1680
agggctattg aggcgcaaca gcatctgttg caactcacag tctggggcat caagcagctc   1740
caggcaagag tcctggctgt ggaaagatac ctacgtgatc aacagctcct gggaatttgg   1800
ggttgctctg gaaaactcat ctgcaccact gctgtgcctt ggaatgttag ttggaataat   1860
agatctgtgg atgacatttg ggaaaacatg acctggatgc agtgggatag agaaattagt   1920
aattacacaa gtttaatata caccttaatt gaagaatcgc agaatcagca agaaaagaat   1980
```

-continued

```
gaacaagaat tattggcatt agataaatgg gcaaatttgt ggaattggtt caacataaca   2040

gaatggctgt ggtatataaa aatattcata atgatagtag gaggcttggt aggtttaaga   2100

atagtttttg ctgtgctttc tatagtgaat agagttaggc agggatactc accattatcg   2160

tttcagaccc acctcccagc tcagagggga cccgacaggc ccggaggaat cgaagaagaa   2220

ggtggagaga gcgacagaga cagatccgga agattagtga atggattctt agcaattatc   2280

tggatcgacc tgcggagcct gtgccttttc agctaccacc acttgagaga cttactattg   2340

attgtaacga ggattgtgga aattctggga cgcagggggt gggaaatcct caagtattgg   2400

tggaatctcc tgcagtattg gattcaggaa ctaaagaata gtgctgttag cttgctcaac   2460

gccatagcca tagcagtagg tgaggggaca gataggatta tagaagcatt tagaagcatt   2520

tttagagcta ttctccacat acctacaaga ataagacagg gcttggaaag gtctttgcta   2580

taa                                                                  2583


<210> SEQ ID NO 2
<211> LENGTH: 860
<212> TYPE: PRT
<213> ORGANISM: Artificial Sequence
<220> FEATURE:
<223> OTHER INFORMATION: Artificially synthesized env polypeptide of the
      HIV AC10 isolate

<400> SEQUENCE: 2

Met Arg Val Arg Glu Thr Arg Lys Asn Tyr Gln His Leu Trp Trp Lys
1               5                   10                  15

Trp Gly Met Met Leu Leu Gly Met Leu Met Ile Cys Ser Ala Val Glu
            20                  25                  30

Gln Thr Trp Val Thr Val Tyr Tyr Gly Val Pro Val Trp Lys Glu Ala
        35                  40                  45

Asn Thr Ile Leu Phe Cys Ala Ser Asp Ala Lys Ala Tyr Asn Thr Glu
    50                  55                  60

Val His Asn Val Trp Ala Thr His Ala Cys Val Pro Thr Asp Pro Asn
65                  70                  75                  80

Pro Gln Glu Val Glu Leu Glu Asn Val Thr Glu Asn Phe Asn Met Trp
                85                  90                  95

Lys Asn Asn Met Val Asp Gln Met His Gly Asp Ile Ile Ser Leu Trp
            100                 105                 110

Asp Gln Ser Leu Lys Pro Cys Val Lys Leu Thr Pro Leu Cys Val Thr
        115                 120                 125

Leu Ser Cys Thr Asp Asn Val Gly Asn Asp Thr Ser Thr Asn Asn Ser
    130                 135                 140

Arg Trp Asp Lys Met Glu Lys Gly Glu Ile Lys Asn Cys Ser Phe Asn
145                 150                 155                 160

Ile Thr Thr Asn Met Arg Asp Lys Met Gln Lys Gln Tyr Ala Leu Phe
                165                 170                 175

Tyr Lys Leu Asp Val Val Pro Ile Glu Glu Gly Lys Asn Asn Asn Ser
            180                 185                 190

Ser Phe Thr Asp Tyr Arg Leu Ile Ser Cys Asn Thr Ser Val Ile Thr
        195                 200                 205

Gln Ala Cys Pro Lys Val Thr Phe Glu Pro Ile Pro Ile His Tyr Cys
    210                 215                 220

Ala Pro Ala Gly Phe Ala Leu Leu Lys Cys Lys Asp Lys Lys Phe Asn
225                 230                 235                 240

Gly Thr Gly Pro Cys Lys Asn Val Ser Thr Val Gln Cys Thr His Gly
```

-continued

```
                245                 250                 255

Ile Lys Pro Val Val Ser Thr Gln Leu Leu Leu Asn Gly Ser Leu Ala
            260                 265                 270

Glu Glu Glu Val Val Ile Arg Ser Glu Asn Phe Ser Asn Asn Ala Arg
        275                 280                 285

Thr Ile Ile Val Gln Leu Asn Thr Ser Val Glu Ile Lys Cys Ile Arg
    290                 295                 300

Pro Asn Asn Asn Thr Arg Lys Gly Ile His Ile Gly Pro Gly Arg Ala
305                 310                 315                 320

Phe Tyr Thr Thr Gly Asp Ile Ile Gly Asp Ile Arg Gln Ala His Cys
                325                 330                 335

Asn Ile Ser Arg Gln Asn Trp Asn Asn Thr Leu Lys Gln Ile Ala Glu
            340                 345                 350

Lys Leu Arg Glu Gln Phe Gly Asn Lys Thr Ile Val Phe Arg Asn Ser
        355                 360                 365

Ser Gly Gly Asp Pro Glu Ile Val Met His Thr Phe Asn Cys Ala Gly
    370                 375                 380

Glu Phe Phe Tyr Cys Asn Thr Ala Glu Leu Phe Asn Ser Thr Trp Tyr
385                 390                 395                 400

Ala Asn Gly Thr Ile Ser Ile Gly Gly Gly Asn Lys Thr Asn Ile Ile
                405                 410                 415

Leu Pro Cys Arg Ile Lys Gln Phe Ile Asn Met Trp Gln Glu Val Gly
            420                 425                 430

Lys Ala Met Tyr Ala Pro Pro Ile Ser Gly Gln Ile Arg Cys Ser Ser
        435                 440                 445

Asn Ile Thr Gly Leu Leu Leu Thr Arg Asp Gly Gly Arg Gly Asn Gln
    450                 455                 460

Thr Asp Asn Gln Thr Glu Ile Phe Arg Pro Val Gly Gly Asp Met Lys
465                 470                 475                 480

Asn Asn Trp Arg Ser Glu Leu Tyr Lys Tyr Lys Val Val Arg Ile Glu
                485                 490                 495

Pro Leu Gly Ile Ala Pro Thr Arg Ala Lys Arg Arg Val Val Gln Arg
            500                 505                 510

Glu Lys Arg Ala Val Gly Ile Gly Ala Leu Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Leu Leu Leu Ser Gly Ile Val Gln Gln Gln Asn Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Gly Lys Leu Ile Cys
        595                 600                 605

Thr Thr Ala Val Pro Trp Asn Val Ser Trp Asn Asn Arg Ser Val Asp
    610                 615                 620

Asp Ile Trp Glu Asn Met Thr Trp Met Gln Trp Asp Arg Glu Ile Ser
625                 630                 635                 640

Asn Tyr Thr Ser Leu Ile Tyr Thr Leu Ile Glu Glu Ser Gln Asn Gln
                645                 650                 655

Gln Glu Lys Asn Glu Gln Glu Leu Leu Ala Leu Asp Lys Trp Ala Asn
            660                 665                 670
```

```
Leu Trp Asn Trp Phe Asn Ile Thr Glu Trp Leu Trp Tyr Ile Lys Ile
        675                 680                 685

Phe Ile Met Ile Val Gly Gly Leu Val Gly Leu Arg Ile Val Phe Ala
    690                 695                 700

Val Leu Ser Ile Val Asn Arg Val Arg Gln Gly Tyr Ser Pro Leu Ser
705                 710                 715                 720

Phe Gln Thr His Leu Pro Ala Gln Arg Gly Pro Asp Arg Pro Gly Gly
                725                 730                 735

Ile Glu Glu Glu Gly Gly Glu Ser Asp Arg Asp Arg Ser Gly Arg Leu
            740                 745                 750

Val Asn Gly Phe Leu Ala Ile Ile Trp Ile Asp Leu Arg Ser Leu Cys
        755                 760                 765

Leu Phe Ser Tyr His His Leu Arg Asp Leu Leu Leu Ile Val Thr Arg
    770                 775                 780

Ile Val Glu Ile Leu Gly Arg Arg Gly Trp Glu Ile Leu Lys Tyr Trp
785                 790                 795                 800

Trp Asn Leu Leu Gln Tyr Trp Ile Gln Glu Leu Lys Asn Ser Ala Val
                805                 810                 815

Ser Leu Leu Asn Ala Ile Ala Ile Ala Val Gly Glu Gly Thr Asp Arg
            820                 825                 830

Ile Ile Glu Ala Phe Arg Ser Ile Phe Arg Ala Ile Leu His Ile Pro
        835                 840                 845

Thr Arg Ile Arg Gln Gly Leu Glu Arg Ser Leu Leu
    850                 855                 860
```

<210> SEQ ID NO 3
<211> LENGTH: 2583
<212> TYPE: DNA
<213> ORGANISM: Artificial Sequence
<220> FEATURE:
<223> OTHER INFORMATION: Artificially synthesized polynucleotide encoding a fragment of env polypeptide of the LR1-C1 isolate

<400> SEQUENCE: 3

```
atgagagtga gggagaccag gaagaattat cagcacttgt ggtggaaatg gggcatgatg     60
ctccttggga tgttgatgat ctgtagtgct gtagaacaaa cgtgggtcac agtctattat    120
ggggtacctg tgtggaaaga agcaaacacc attttatttt gtgcatcaga tgctaaagca    180
tataatacag aggtacataa tgtttgggcc acacatgcct gtgtacccac agaccccaac    240
ccacaagaag tagaattgga agatgtgaca gaaaatttta acatgtggaa aaacaacatg    300
gtagatcaga tgcatgggga tataatcagt ttatgggatc aaagcctaaa gccatgtgta    360
aaattaactc cactctgtgt tactttaagt tacaatgata atgtgggaaa tggtactagt    420
accaataata gtagatggga taaaatggaa aaaggagaaa taaagaactg ctctttctat    480
atcaccacaa acatgagaga taagatgcag aaacaatatg cactttttta taaacttgat    540
gtagtaccaa tagaggaagg taagaataat gacagtagtt ttaccgacta taggttgata    600
agttgtaaca cctcagtcat tacacaggcc tgtccaaagg taacctttga gccaattccc    660
atacattatt gtgtcccagc tggttttgcg cttctaaaat gtaaggataa gaaattcaat    720
ggaacaggac catgtaaaaa tgttagcaca gtacaatgta cacatggaat taagccagta    780
gtatcaactc agctgctatt aaatggcagt ctagcagaag aagaggtagt aataagatct    840
gagaacttct cgaacaatgc tagaaccata atagtacagc tgaatacatc tgtagaaata    900
aagtgtataa gacccaacaa caatacaaga aaaggtatac atataggacc agggagagca    960
```

-continued ttttatacaa caggagatat aataggagat ataagacaag cacattgtaa cattagtaga 1020
caaaattgga ataacacttt aaaacagata gctgaaaagt taagagaaca atttgggaat 1080
aaaacaatag tctttagaaa ctcctctgga ggggatccag aaattgtaat gcacactttt 1140
aattgtgcag gggaattttt ctactgtaat acagcagaac tgtttaatag tacttggtat 1200
gcaaatggca caattagtat tggagggga aacaagacta atatcatact cccatgcaga 1260
ataaaacaat ttataaacat gtggcaagaa gtaggaaaag caatgtatgc ccctcccatc 1320
agtggacaga ttagatgttc atcaaatatt acaggactgc tattaacaag agatggtggt 1380
aggggcaatc agaccgacaa ccagactgag atcttcagac ctgtaggagg agatataaaa 1440
aacaattgga gaagtgaatt atataaatat aaagtagtaa gaattgaacc attaggaata 1500
gcacccacca gggcaaaatg gagagtggtg cagagagaaa aaagagcagt gggaatagga 1560
gctttgttcc ttgggttctt gggagcagca ggaagcacta tgggcgcagc gtcaatgacg 1620
ctgacggtac aggccagact attattgtct ggtatagtgc aacagcagaa caatctgctg 1680
agggctattg aggcgcaaca gcatctgttg caactcacag tctggggcat caagcagctc 1740
caggcaagag tcctggctgt ggaaagatac ctacgtgatc aacagctcct gggaatttgg 1800
ggttgctctg gaaaactcat ctgcaccact gctgtgcctt ggaatgttag ttggaataat 1860
agatctgtgg atgacatttg ggaaaacatg acctggatgc agtgggatag agaaattagt 1920
aattacacaa gtttaataaa caccttaatt gaagaatcgc agaatcagca agaaaagaat 1980
gaacaagaat tattggcatt agataaatgg gcaaatttgt ggaattggtt caacataaca 2040
gaatggctgt ggtatataaa aatattcata atgatagtag gaggcttggt aggtttaaga 2100
atagtttttg ctgtgctttc tatagtgaat agagttaggc agggatactc accattatcg 2160
tttcagaccc acctcccagc tcagagggga cccgacaggc ccggaggaat cgaagaagaa 2220
ggtggagaga gcgacagaga cagatccgga agattagtga atggattctt agcaattatc 2280
tggatcgacc tgcggagcct gtgccttttc agctaccacc acttgagaga cttactattg 2340
attgtaacga ggattgtgga aattctggga cgcagggggt gggaaatcct caagtattgg 2400
tggaatctcc tgcagtattg gattcaggaa ctaaagaata gtgctgttag cttgctcaac 2460
gccatagcca tagcagtagg tgaggggaca gataggatta tagaagcatt tagaagcatt 2520
tttagagcta ttctccacat acctacaaga ataagacagg gcttggaaag gtctttgcta 2580
taa 2583

<210> SEQ ID NO 4
<211> LENGTH: 860
<212> TYPE: PRT
<213> ORGANISM: Artificial Sequence
<220> FEATURE:
<223> OTHER INFORMATION: Artificially synthesized env polypeptide of the
LR1-C1 isolate

<400> SEQUENCE: 4

Met Arg Val Arg Glu Thr Arg Lys Asn Tyr Gln His Leu Trp Trp Lys
1 5 10 15

Trp Gly Met Met Leu Leu Gly Met Leu Met Ile Cys Ser Ala Val Glu
20 25 30

Gln Thr Trp Val Thr Val Tyr Tyr Gly Val Pro Val Trp Lys Glu Ala
35 40 45

Asn Thr Ile Leu Phe Cys Ala Ser Asp Ala Lys Ala Tyr Asn Thr Glu
50 55 60

```
Val His Asn Val Trp Ala Thr His Ala Cys Val Pro Thr Asp Pro Asn
65                  70                  75                  80

Pro Gln Glu Val Glu Leu Glu Asp Val Thr Glu Asn Phe Asn Met Trp
                85                  90                  95

Lys Asn Asn Met Val Asp Gln Met His Gly Asp Ile Ile Ser Leu Trp
            100                 105                 110

Asp Gln Ser Leu Lys Pro Cys Val Lys Leu Thr Pro Leu Cys Val Thr
        115                 120                 125

Leu Ser Tyr Asn Asp Asn Val Gly Asn Gly Thr Ser Thr Asn Asn Ser
    130                 135                 140

Arg Trp Asp Lys Met Glu Lys Gly Glu Ile Lys Asn Cys Ser Phe Tyr
145                 150                 155                 160

Ile Thr Thr Asn Met Arg Asp Lys Met Gln Lys Gln Tyr Ala Leu Phe
                165                 170                 175

Tyr Lys Leu Asp Val Val Pro Ile Glu Glu Gly Lys Asn Asn Asp Ser
            180                 185                 190

Ser Phe Thr Asp Tyr Arg Leu Ile Ser Cys Asn Thr Ser Val Ile Thr
        195                 200                 205

Gln Ala Cys Pro Lys Val Thr Phe Glu Pro Ile Pro Ile His Tyr Cys
    210                 215                 220

Val Pro Ala Gly Phe Ala Leu Leu Lys Cys Lys Asp Lys Lys Phe Asn
225                 230                 235                 240

Gly Thr Gly Pro Cys Lys Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Val Val Ile Arg Ser Glu Asn Phe Ser Asn Asn Ala Arg
        275                 280                 285

Thr Ile Ile Val Gln Leu Asn Thr Ser Val Glu Ile Lys Cys Ile Arg
    290                 295                 300

Pro Asn Asn Asn Thr Arg Lys Gly Ile His Ile Gly Pro Gly Arg Ala
305                 310                 315                 320

Phe Tyr Thr Thr Gly Asp Ile Ile Gly Asp Ile Arg Gln Ala His Cys
                325                 330                 335

Asn Ile Ser Arg Gln Asn Trp Asn Asn Thr Leu Lys Gln Ile Ala Glu
            340                 345                 350

Lys Leu Arg Glu Gln Phe Gly Asn Lys Thr Ile Val Phe Arg Asn Ser
        355                 360                 365

Ser Gly Gly Asp Pro Glu Ile Val Met His Thr Phe Asn Cys Ala Gly
    370                 375                 380

Glu Phe Phe Tyr Cys Asn Thr Ala Glu Leu Phe Asn Ser Thr Trp Tyr
385                 390                 395                 400

Ala Asn Gly Thr Ile Ser Ile Gly Gly Gly Asn Lys Thr Asn Ile Ile
                405                 410                 415

Leu Pro Cys Arg Ile Lys Gln Phe Ile Asn Met Trp Gln Glu Val Gly
            420                 425                 430

Lys Ala Met Tyr Ala Pro Pro Ile Ser Gly Gln Ile Arg Cys Ser Ser
        435                 440                 445

Asn Ile Thr Gly Leu Leu Leu Thr Arg Asp Gly Gly Arg Gly Asn Gln
    450                 455                 460

Thr Asp Asn Gln Thr Glu Ile Phe Arg Pro Val Gly Gly Asp Ile Lys
465                 470                 475                 480
```

-continued

```
Asn Asn Trp Arg Ser Glu Leu Tyr Lys Tyr Lys Val Val Arg Ile Glu
                485                 490                 495

Pro Leu Gly Ile Ala Pro Thr Arg Ala Lys Trp Arg Val Val Gln Arg
            500                 505                 510

Glu Lys Arg Ala Val Gly Ile Gly Ala Leu Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Leu Leu Leu Ser Gly Ile Val Gln Gln Gln Asn Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Gly Lys Leu Ile Cys
        595                 600                 605

Thr Thr Ala Val Pro Trp Asn Val Ser Trp Asn Asn Arg Ser Val Asp
    610                 615                 620

Asp Ile Trp Glu Asn Met Thr Trp Met Gln Trp Asp Arg Glu Ile Ser
625                 630                 635                 640

Asn Tyr Thr Ser Leu Ile Asn Thr Leu Ile Glu Glu Ser Gln Asn Gln
                645                 650                 655

Gln Glu Lys Asn Glu Gln Glu Leu Leu Ala Leu Asp Lys Trp Ala Asn
            660                 665                 670

Leu Trp Asn Trp Phe Asn Ile Thr Glu Trp Leu Trp Tyr Ile Lys Ile
        675                 680                 685

Phe Ile Met Ile Val Gly Gly Leu Val Gly Leu Arg Ile Val Phe Ala
    690                 695                 700

Val Leu Ser Ile Val Asn Arg Val Arg Gln Gly Tyr Ser Pro Leu Ser
705                 710                 715                 720

Phe Gln Thr His Leu Pro Ala Gln Arg Gly Pro Asp Arg Pro Gly Gly
                725                 730                 735

Ile Glu Glu Glu Gly Gly Glu Ser Asp Arg Asp Arg Ser Gly Arg Leu
            740                 745                 750

Val Asn Gly Phe Leu Ala Ile Ile Trp Ile Asp Leu Arg Ser Leu Cys
        755                 760                 765

Leu Phe Ser Tyr His His Leu Arg Asp Leu Leu Leu Ile Val Thr Arg
    770                 775                 780

Ile Val Glu Ile Leu Gly Arg Arg Gly Trp Glu Ile Leu Lys Tyr Trp
785                 790                 795                 800

Trp Asn Leu Leu Gln Tyr Trp Ile Gln Glu Leu Lys Asn Ser Ala Val
                805                 810                 815

Ser Leu Leu Asn Ala Ile Ala Ile Ala Val Gly Glu Gly Thr Asp Arg
            820                 825                 830

Ile Ile Glu Ala Phe Arg Ser Ile Phe Arg Ala Ile Leu His Ile Pro
        835                 840                 845

Thr Arg Ile Arg Gln Gly Leu Glu Arg Ser Leu Leu
    850                 855                 860
```

<210> SEQ ID NO 5
<211> LENGTH: 25
<212> TYPE: DNA
<213> ORGANISM: Artificial Sequence
<220> FEATURE:
<223> OTHER INFORMATION: Artificially synthesized oligonucleotide primer aligning with a fragment of the HIV-1 HXB2 genome

<400> SEQUENCE: 5
tagagccctg gaagcatcca ggaag 25

<210> SEQ ID NO 6
<211> LENGTH: 24
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 6
ttgctacttg tgattgctcc atgt 24

<210> SEQ ID NO 7
<211> LENGTH: 33
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 7
agctggatcc gtctcgagat actgctccca ccc 33

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 8
gtagtacatg taatgcaacc 20

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 9
agctcgtctc attctttccc 20

<210> SEQ ID NO 10
<211> LENGTH: 23
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 10
ccaattccca tacattattg tgc 23

<210> SEQ ID NO 11
<211> LENGTH: 24
<212> TYPE: DNA
<213> ORGANISM: Artificial Sequence
<220> FEATURE:
<223> OTHER INFORMATION: Artificially synthesized oligonucleotide primer
aligning with a fragment of the HIV-1 HXB2 genome

<400> SEQUENCE: 11
ggagcagcag gaagcactat gggc 24

<210> SEQ ID NO 12
<211> LENGTH: 22
<212> TYPE: DNA
<213> ORGANISM: Artificial Sequence
<220> FEATURE:
<223> OTHER INFORMATION: Artificially synthesized oligonucleotide primer aligning with a fragment of the HIV-1 HXB2 genome

<400> SEQUENCE: 12
gagttaggca gggatactca cc 22

<210> SEQ ID NO 13
<211> LENGTH: 23
<212> TYPE: DNA
<213> ORGANISM: Artificial Sequence
<220> FEATURE:
<223> OTHER INFORMATION: Artificially synthesized oligonucleotide primer aligning with a fragment of the HIV-1 HXB2 genome

<400> SEQUENCE: 13
gccaggactc ttgcctggag ctg 23

<210> SEQ ID NO 14
<211> LENGTH: 19
<212> TYPE: DNA
<213> ORGANISM: Artificial Sequence
<220> FEATURE:
<223> OTHER INFORMATION: Artificially synthesized oligonucleotide primer aligning with a fragment of the HIV-1 HXB2 genome

<400> SEQUENCE: 14
cttgtattgt tgttgggtc 19

<210> SEQ ID NO 15
<211> LENGTH: 22
<212> TYPE: DNA
<213> ORGANISM: Artificial Sequence
<220> FEATURE:
<223> OTHER INFORMATION: Artificially synthesized oligonucleotide primer aligning with a fragment of the HIV-1 HXB2 genome

<400> SEQUENCE: 15
catggcttta ggctttgatc cc 22

<210> SEQ ID NO 16
<211> LENGTH: 103
<212> TYPE: PRT
<213> ORGANISM: Artificial Sequence
<220> FEATURE:
<223> OTHER INFORMATION: Artificially synthesized peptide fragment of gp160 preprotein encoded by the env gene of the HIV AC10 wild-type isolate

<400> SEQUENCE: 16

```
Gln Ser Leu Lys Pro Cys Val Lys Leu Thr Pro Leu Cys Val Thr Leu
1               5                   10                  15

Ser Cys Thr Asp Asn Val Gly Asn Asp Thr Ser Thr Asn Asn Ser Arg
            20                  25                  30

Trp Asp Lys Met Glu Lys Gly Glu Ile Lys Asn Cys Ser Phe Asn Ile
        35                  40                  45

Thr Thr Asn Met Arg Asp Lys Met Gln Lys Gln Tyr Ala Leu Phe Tyr
```

```
    50                  55                  60

Lys Leu Asp Val Val Pro Ile Glu Glu Gly Lys Asn Asn Asn Ser Ser
65                  70                  75                  80

Phe Thr Asp Tyr Arg Leu Ile Ser Cys Asn Thr Ser Val Ile Thr Gln
                85                  90                  95

Ala Cys Pro Lys Val Thr Phe
            100


<210> SEQ ID NO 17
<211> LENGTH: 103
<212> TYPE: PRT
<213> ORGANISM: Artificial Sequence
<220> FEATURE:
<223> OTHER INFORMATION: Artificially synthesized peptide fragment of
      env polypeptide of the LR1-C1 isolate

<400> SEQUENCE: 17

Gln Ser Leu Lys Pro Cys Val Lys Leu Thr Pro Leu Cys Val Thr Leu
1               5                   10                  15

Ser Tyr Asn Asp Asn Val Gly Asn Gly Thr Ser Thr Asn Asn Ser Arg
            20                  25                  30

Trp Asp Lys Met Glu Lys Gly Glu Ile Lys Asn Cys Ser Phe Tyr Ile
        35                  40                  45

Thr Thr Asn Met Arg Asp Lys Met Gln Lys Gln Tyr Ala Leu Phe Tyr
    50                  55                  60

Lys Leu Asp Val Val Pro Ile Glu Glu Gly Lys Asn Asn Asp Ser Ser
65                  70                  75                  80

Phe Thr Asp Tyr Arg Leu Ile Ser Cys Asn Thr Ser Val Ile Thr Gln
                85                  90                  95

Ala Cys Pro Lys Val Thr Phe
            100


<210> SEQ ID NO 18
<211> LENGTH: 40
<212> TYPE: PRT
<213> ORGANISM: Artificial Sequence
<220> FEATURE:
<223> OTHER INFORMATION: Artificially synthesized peptide ENV AC10
      sequenced fragment

<400> SEQUENCE: 18

Lys Leu Thr Pro Leu Cys Val Thr Leu Ser Cys Thr Asp Asn Val Gly
1               5                   10                  15

Asn Asp Thr Ser Thr Asn Asn Ser Arg Trp Asp Lys Met Glu Lys Gly
            20                  25                  30

Glu Ile Lys Asn Cys Ser Phe Asn
        35                  40


<210> SEQ ID NO 19
<211> LENGTH: 40
<212> TYPE: PRT
<213> ORGANISM: Artificial Sequence
<220> FEATURE:
<223> OTHER INFORMATION: Artificially synthesized peptide L1-1 contig
      ENV

<400> SEQUENCE: 19

Lys Leu Thr Pro Leu Cys Val Thr Leu Ser Cys Thr Asp Asn Val Gly
1               5                   10                  15

Asn Asp Thr Ser Thr Asn Asn Ser Arg Trp Asp Lys Met Glu Lys Gly
            20                  25                  30
```

```
Glu Ile Lys Asn Cys Tyr Phe Asn
        35                  40


<210> SEQ ID NO 20
<211> LENGTH: 40
<212> TYPE: PRT
<213> ORGANISM: Artificial Sequence
<220> FEATURE:
<223> OTHER INFORMATION: Artificially synthesized peptide L1-2 contig
      ENV

<400> SEQUENCE: 20

Lys Leu Thr Gln Leu Cys Asp Thr Leu Ser Cys Thr Asp Asn Val Gly
1               5                   10                  15

Asn Asp Thr Ser Thr Asn Asn Ser Arg Trp Asp Lys Met Glu Lys Gly
            20                  25                  30

Glu Ile Lys Asn Cys Ser Phe Asn
        35                  40


<210> SEQ ID NO 21
<211> LENGTH: 40
<212> TYPE: PRT
<213> ORGANISM: Artificial Sequence
<220> FEATURE:
<223> OTHER INFORMATION: Artificially synthesized oligonucleotide L1-3
      contig ENV

<400> SEQUENCE: 21

Lys Leu Thr Pro Leu Cys Val Thr Leu Ser Cys Thr Asp Asn Glu Gly
1               5                   10                  15

Asn Asp Thr Ser Thr Asn Asn Ser Arg Trp Asp Lys Met Gly Lys Gly
            20                  25                  30

Glu Ile Lys Asn Cys Ser Phe Asn
        35                  40


<210> SEQ ID NO 22
<211> LENGTH: 40
<212> TYPE: PRT
<213> ORGANISM: Artificial Sequence
<220> FEATURE:
<223> OTHER INFORMATION: Artificially synthesized peptide L1-6 contig
      ENV
<220> FEATURE:
<221> NAME/KEY: MISC_FEATURE
<222> LOCATION: (29)..(29)
<223> OTHER INFORMATION: Xaa can be any amino acid

<400> SEQUENCE: 22

Lys Leu Thr Pro Leu Cys Val Thr Leu Ser Cys Thr Asp Asn Val Gly
1               5                   10                  15

Asn Asp Thr Ser Thr Asn Asn Ser Arg Trp Asp Lys Xaa Glu Lys Gly
            20                  25                  30

Glu Ile Lys Asn Cys Ser Phe Asn
        35                  40


<210> SEQ ID NO 23
<211> LENGTH: 40
<212> TYPE: PRT
<213> ORGANISM: Artificial Sequence
<220> FEATURE:
<223> OTHER INFORMATION: Artificially synthesized peptide L2-2 contig
      ENV
<220> FEATURE:
<221> NAME/KEY: MISC_FEATURE
<222> LOCATION: (35)..(35)
```

<223> OTHER INFORMATION: Xaa can be any amino acid

<400> SEQUENCE: 23

```
Lys Leu Thr Pro Leu Cys Val Thr Leu Ser Cys Thr Asp Asn Val Gly
1               5                   10                  15

Asn Asp Thr Ser Thr Asn Asn Ser Arg Trp Asp Lys Met Glu Lys Gly
            20                  25                  30

Glu Ile Xaa Asn Cys Ser Phe Asn
        35                  40
```

<210> SEQ ID NO 24
<211> LENGTH: 40
<212> TYPE: PRT
<213> ORGANISM: Artificial Sequence
<220> FEATURE:
<223> OTHER INFORMATION: Artificially synthesized oligonucleotide L2-3 contig ENV

<400> SEQUENCE: 24

```
Lys Leu Thr Pro Leu Cys Val Thr Leu Ser Cys Thr Asp Asn Val Gly
1               5                   10                  15

Asn Asp Ile Ser Thr Ile Asn Ser Arg Trp Asp Lys Met Glu Lys Gly
            20                  25                  30

Glu Ile Lys Asn Cys Ser Cys Asn
        35                  40
```

<210> SEQ ID NO 25
<211> LENGTH: 40
<212> TYPE: PRT
<213> ORGANISM: Artificial Sequence
<220> FEATURE:
<223> OTHER INFORMATION: Artificially synthesized oligonucleotide L3-4 contig ENV

<400> SEQUENCE: 25

```
Lys Leu Thr Pro Leu Cys Val Thr Leu Ser Cys Thr Asp Asn Met Gly
1               5                   10                  15

Asn Asp Thr Ser Thr Asn Asn Ser Arg Trp Asp Lys Met Glu Lys Gly
            20                  25                  30

Glu Ile Lys Asn Cys Ser Phe Asn
        35                  40
```

<210> SEQ ID NO 26
<211> LENGTH: 40
<212> TYPE: PRT
<213> ORGANISM: Artificial Sequence
<220> FEATURE:
<223> OTHER INFORMATION: Artificially synthesized oligonucleotide Contig L2 clone 5 pNL43

<400> SEQUENCE: 26

```
Lys Leu Thr Pro Leu Cys Val Thr Leu Ser Cys Thr Asp Asn Val Gly
1               5                   10                  15

Asn Asp Thr Ser Thr Asn Asn Ser Arg Trp Asp Lys Met Glu Lys Gly
            20                  25                  30

Glu Ile Lys Asn Phe Ser Phe Asn
        35                  40
```

<210> SEQ ID NO 27
<211> LENGTH: 40
<212> TYPE: PRT
<213> ORGANISM: Artificial Sequence
<220> FEATURE:

-continued

<223> OTHER INFORMATION: Artificially synthesized oligonucleotide Contig
      BR1 clone 1 pcDNA

<400> SEQUENCE: 27

Lys Leu Thr Pro Leu Cys Val Thr Leu Ser Tyr Asn Asp Asn Val Gly
1               5                   10                  15

Asn Asp Thr Ser Thr Asn Asn Ser Arg Trp Asp Lys Met Glu Lys Gly
            20                  25                  30

Glu Ile Lys Asn Cys Ser Phe Asn
        35                  40

<210> SEQ ID NO 28
<211> LENGTH: 40
<212> TYPE: PRT
<213> ORGANISM: Artificial Sequence
<220> FEATURE:
<223> OTHER INFORMATION: Artificially synthesized oligonucleotide Contig
      BR1 clone 3 pcDNA

<400> SEQUENCE: 28

Lys Leu Thr Pro Leu Cys Val Thr Leu Ser Tyr Lys Asp Asn Val Gly
1               5                   10                  15

Asn Asp Thr Ser Thr Asn Asn Ser Arg Trp Asp Lys Met Glu Lys Gly
            20                  25                  30

Glu Ile Lys Asn Cys Ser Phe Asn
        35                  40

<210> SEQ ID NO 29
<211> LENGTH: 40
<212> TYPE: PRT
<213> ORGANISM: Artificial Sequence
<220> FEATURE:
<223> OTHER INFORMATION: Artificially synthesized oligonucleotide Contig
      BR1 clone 1

<400> SEQUENCE: 29

Lys Leu Thr Pro Leu Cys Val Thr Leu Ser Tyr Asn Asp Asn Val Gly
1               5                   10                  15

Asn Asp Gly Ser Thr Asn Asn Ser Arg Trp Asp Lys Met Glu Lys Gly
            20                  25                  30

Glu Ile Lys Asn Cys Ser Phe Tyr
        35                  40

<210> SEQ ID NO 30
<211> LENGTH: 2583
<212> TYPE: DNA
<213> ORGANISM: Artificial Sequence
<220> FEATURE:
<223> OTHER INFORMATION: Artificially synthesized oligonucleotide Env
      nucleotide sequence selected with PG16-C10 antibody

<400> SEQUENCE: 30
atgagagtga gggagaccag gaagaattat cagcacttgt ggtggaaatg gggcatgatg     60
ctccttggga tgttgatgat ctgtagtgct gtagaacaaa cgtgggtcac agtctattat    120
ggggtacctg tgtggaaaga agcaaacacc attttatttt gtgcatcaga tgctaaagca    180
tataatacag aggtacataa tgtttgggcc acacatgcct gtgtacccac agaccccaac    240
ccacaagaag tagaattgga aaatgtgaca gaaaatttta acatgtggaa aaacaacatg    300
gtagatcaga tgcatgggga tataatcagt ttatgggatc aaagcctaaa gccatgtgta    360
aaattaactc cactctgtgt tactttaagt tgcactgata atgtgggaaa tgatactagt    420

-continued

```
accaataata gtagatggga taaaatggaa aaaggagaaa taaagaactg ctctttcaat    480
atcaccacaa acatgagaga taagatgcag aaacaatatg cacttttta taaacttgat    540
gtagtaccaa tagaggaagg taagaataat aacagtagtt ttaccgacta taggttgata    600
agttgtagca cctcagtcat tacacaggcc tgtccaaagg taacctttga gccaattccc    660
atacattatt gtgccccagc tggttttgcg cttctaaaat gtaaggataa gaaattcaat    720
ggaaccggac catgtaaaaa tgttagcaca gtacaatgta cacatggaat taagccagta    780
gtatcaactc agctgctatt aaatggcagt ctagcagaag aagaggtagt aataagatct    840
gagaacttct cgaacaatgc tagaaccata atagtacagc tgaatacatc tgtagaaata    900
aagtgtataa gacccaacaa caatacaaga aaaggtatac atataggacc agggagagca    960
ttttatacaa caggagatat aataggagat ataagacaag cacattgtaa cattagtaga   1020
caaaattgga ataacacttt aaaacagata gctgaaaagt taagagaaca atttgggaat   1080
aaaacaatag tctttagaaa ctcctctgga ggggatccag aaattgtaat gcacactttt   1140
aattgtgcag gggaattttt ctactgtaat acagcagaac tgtttaatag tacttggtat   1200
gcaaatggca caattagtat tggagggggga aacaagacta atatcatact cccatgcaga   1260
ataaaacaat ttataaacat gtggcaggaa gtaggaaaag caatgtatgc ccctcccatc   1320
agtggacaga ttagatgttc atcaaatatt acaggactgc tattaacaag agatggtggt   1380
aggggcaatc agaccgacaa ccagactgag atcttcagac ctgtaggagg agatatgaaa   1440
aacaattgga gaagtgaatt atataaatat aaagtagtaa gaattgaacc attaggaata   1500
gcacccacca gggcaaaaag gagagtggtg cagagagaaa aaagagcagt gggaatagga   1560
gctttgttcc ttgggttctt gggagcagca ggaagcacta tgggcgcagc gtcaatgacg   1620
ctgacggtac aggccagact attattgtct ggtatagtgc aacagcagaa caatctgctg   1680
agggctattg aggcgcaaca gcatctgttg caactcacag tctggggcat caagcagctc   1740
caggcaagag tcctggctgt ggaaagatac ctacgtgatc aacagctcct gggaatttgg   1800
ggttgctctg aaaaactcat ctgcaccact gctgtgcctt ggaatgttag ttggaataat   1860
agatctgtgg atgacatttg ggaaaacatg acctggatgc agtgggatag agaaattagt   1920
aattacacaa gtttaatata caccttaatt gaagaatcgc agaatcagca agaaaagaat   1980
gaacaagaat tattggcatt agataaatgg gcaaatttgt ggaattggtt caacataaca   2040
gaatggctgt ggtatataaa aatattcata atgatagtag gaggcttggt aggtttaaga   2100
atagtttttg ctgtgctttc tatagtgaat agagttaggc agggatactc accattatcg   2160
tttcagaccc acctcccagc tcagaggggga cccgacaggc ccggaggaat cgaagaagaa   2220
ggtggagaga gcgacagaga cagatccgga agattagtga atggattctt agcaattatc   2280
tggatcgacc tgcggagcct gtgccttttc agctaccacc acttgagaga cttactattg   2340
attgtaacga ggattgtgga aattctggga cgcagggggt gggaaatcct caagtattgg   2400
tggaatctcc tgcagtattg gattcaggaa ctaaagaata gtgctgttag cctgctcaac   2460
gccatagcca tagcagtagg tgaggggaca gataggatta tagaagcatt tagaagcatt   2520
tttagagcta ttctccacat acctacaaga ataagacagg gcttggaaag gtctttgcta   2580
taa                                                                 2583
```

<210> SEQ ID NO 31
<211> LENGTH: 860
<212> TYPE: PRT
<213> ORGANISM: Artificial Sequence

```
<220> FEATURE:
<223> OTHER INFORMATION: Artificially synthesized oligonucleotide PG16
      clone 10

<400> SEQUENCE: 31

Met Arg Val Arg Glu Thr Arg Lys Asn Tyr Gln His Leu Trp Trp Lys
1               5                   10                  15

Trp Gly Met Met Leu Leu Gly Met Leu Met Ile Cys Ser Ala Val Glu
            20                  25                  30

Gln Thr Trp Val Thr Val Tyr Tyr Gly Val Pro Val Trp Lys Glu Ala
        35                  40                  45

Asn Thr Ile Leu Phe Cys Ala Ser Asp Ala Lys Ala Tyr Asn Thr Glu
    50                  55                  60

Val His Asn Val Trp Ala Thr His Ala Cys Val Pro Thr Asp Pro Asn
65                  70                  75                  80

Pro Gln Glu Val Glu Leu Glu Asn Val Thr Glu Asn Phe Asn Met Trp
                85                  90                  95

Lys Asn Asn Met Val Asp Gln Met His Gly Asp Ile Ile Ser Leu Trp
            100                 105                 110

Asp Gln Ser Leu Lys Pro Cys Val Lys Leu Thr Pro Leu Cys Val Thr
        115                 120                 125

Leu Ser Cys Thr Asp Asn Val Gly Asn Asp Thr Ser Thr Asn Asn Ser
    130                 135                 140

Arg Trp Asp Lys Met Glu Lys Gly Glu Ile Lys Asn Cys Ser Phe Asn
145                 150                 155                 160

Ile Thr Thr Asn Met Arg Asp Lys Met Gln Lys Gln Tyr Ala Leu Phe
                165                 170                 175

Tyr Lys Leu Asp Val Val Pro Ile Glu Glu Gly Lys Asn Asn Asn Ser
            180                 185                 190

Ser Phe Thr Asp Tyr Arg Leu Ile Ser Cys Ser Thr Ser Val Ile Thr
        195                 200                 205

Gln Ala Cys Pro Lys Val Thr Phe Glu Pro Ile Pro Ile His Tyr Cys
    210                 215                 220

Ala Pro Ala Gly Phe Ala Leu Leu Lys Cys Lys Asp Lys Lys Phe Asn
225                 230                 235                 240

Gly Thr Gly Pro Cys Lys Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Val Val Ile Arg Ser Glu Asn Phe Ser Asn Asn Ala Arg
        275                 280                 285

Thr Ile Ile Val Gln Leu Asn Thr Ser Val Glu Ile Lys Cys Ile Arg
    290                 295                 300

Pro Asn Asn Asn Thr Arg Lys Gly Ile His Ile Gly Pro Gly Arg Ala
305                 310                 315                 320

Phe Tyr Thr Thr Gly Asp Ile Ile Gly Asp Ile Arg Gln Ala His Cys
                325                 330                 335

Asn Ile Ser Arg Gln Asn Trp Asn Asn Thr Leu Lys Gln Ile Ala Glu
            340                 345                 350

Lys Leu Arg Glu Gln Phe Gly Asn Lys Thr Ile Val Phe Arg Asn Ser
        355                 360                 365

Ser Gly Gly Asp Pro Glu Ile Val Met His Thr Phe Asn Cys Ala Gly
    370                 375                 380

Glu Phe Phe Tyr Cys Asn Thr Ala Glu Leu Phe Asn Ser Thr Trp Tyr
```

```
385                 390                 395                 400

Ala Asn Gly Thr Ile Ser Ile Gly Gly Gly Asn Lys Thr Asn Ile Ile
                405                 410                 415

Leu Pro Cys Arg Ile Lys Gln Phe Ile Asn Met Trp Gln Glu Val Gly
            420                 425                 430

Lys Ala Met Tyr Ala Pro Pro Ile Ser Gly Gln Ile Arg Cys Ser Ser
        435                 440                 445

Asn Ile Thr Gly Leu Leu Leu Thr Arg Asp Gly Gly Arg Gly Asn Gln
    450                 455                 460

Thr Asp Asn Gln Thr Glu Ile Phe Arg Pro Val Gly Gly Asp Met Lys
465                 470                 475                 480

Asn Asn Trp Arg Ser Glu Leu Tyr Lys Tyr Lys Val Val Arg Ile Glu
                485                 490                 495

Pro Leu Gly Ile Ala Pro Thr Arg Ala Lys Arg Arg Val Val Gln Arg
            500                 505                 510

Glu Lys Arg Ala Val Gly Ile Gly Ala Leu Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Leu Leu Leu Ser Gly Ile Val Gln Gln Gln Asn Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Glu Lys Leu Ile Cys
        595                 600                 605

Thr Thr Ala Val Pro Trp Asn Val Ser Trp Asn Asn Arg Ser Val Asp
    610                 615                 620

Asp Ile Trp Glu Asn Met Thr Trp Met Gln Trp Asp Arg Glu Ile Ser
625                 630                 635                 640

Asn Tyr Thr Ser Leu Ile Tyr Thr Leu Ile Glu Glu Ser Gln Asn Gln
                645                 650                 655

Gln Glu Lys Asn Glu Gln Glu Leu Leu Ala Leu Asp Lys Trp Ala Asn
            660                 665                 670

Leu Trp Asn Trp Phe Asn Ile Thr Glu Trp Leu Trp Tyr Ile Lys Ile
        675                 680                 685

Phe Ile Met Ile Val Gly Gly Leu Val Gly Leu Arg Ile Val Phe Ala
    690                 695                 700

Val Leu Ser Ile Val Asn Arg Val Arg Gln Gly Tyr Ser Pro Leu Ser
705                 710                 715                 720

Phe Gln Thr His Leu Pro Ala Gln Arg Gly Pro Asp Arg Pro Gly Gly
                725                 730                 735

Ile Glu Glu Glu Gly Gly Glu Ser Asp Arg Asp Arg Ser Gly Arg Leu
            740                 745                 750

Val Asn Gly Phe Leu Ala Ile Ile Trp Ile Asp Leu Arg Ser Leu Cys
        755                 760                 765

Leu Phe Ser Tyr His His Leu Arg Asp Leu Leu Leu Ile Val Thr Arg
    770                 775                 780

Ile Val Glu Ile Leu Gly Arg Arg Gly Trp Glu Ile Leu Lys Tyr Trp
785                 790                 795                 800

Trp Asn Leu Leu Gln Tyr Trp Ile Gln Glu Leu Lys Asn Ser Ala Val
                805                 810                 815
```

```
Ser Leu Leu Asn Ala Ile Ala Ile Ala Val Gly Glu Gly Thr Asp Arg
            820                 825                 830

Ile Ile Glu Ala Phe Arg Ser Ile Phe Arg Ala Ile Leu His Ile Pro
        835                 840                 845

Thr Arg Ile Arg Gln Gly Leu Glu Arg Ser Leu Leu
    850                 855                 860


<210> SEQ ID NO 32
<211> LENGTH: 860
<212> TYPE: PRT
<213> ORGANISM: Artificial Sequence
<220> FEATURE:
<223> OTHER INFORMATION: Artificially synthesized oligonucleotide
      Sequence Env AC10

<400> SEQUENCE: 32

Met Arg Val Arg Glu Thr Arg Lys Asn Tyr Gln His Leu Trp Trp Lys
1               5                   10                  15

Trp Gly Met Met Leu Leu Gly Met Leu Met Ile Cys Ser Ala Val Glu
            20                  25                  30

Gln Thr Trp Val Thr Val Tyr Tyr Gly Val Pro Val Trp Lys Glu Ala
        35                  40                  45

Asn Thr Ile Leu Phe Cys Ala Ser Asp Ala Lys Ala Tyr Asn Thr Glu
    50                  55                  60

Val His Asn Val Trp Ala Thr His Ala Cys Val Pro Thr Asp Pro Asn
65                  70                  75                  80

Pro Gln Glu Val Glu Leu Glu Asn Val Thr Glu Asn Phe Asn Met Trp
                85                  90                  95

Lys Asn Asn Met Val Asp Gln Met His Gly Asp Ile Ile Ser Leu Trp
            100                 105                 110

Asp Gln Ser Leu Lys Pro Cys Val Lys Leu Thr Pro Leu Cys Val Thr
        115                 120                 125

Leu Ser Cys Thr Asp Asn Val Gly Asn Asp Thr Ser Thr Asn Asn Ser
    130                 135                 140

Arg Trp Asp Lys Met Glu Lys Gly Glu Ile Lys Asn Cys Ser Phe Asn
145                 150                 155                 160

Ile Thr Thr Asn Met Arg Asp Lys Met Gln Lys Gln Tyr Ala Leu Phe
                165                 170                 175

Tyr Lys Leu Asp Val Val Pro Ile Glu Glu Gly Lys Asn Asn Asn Ser
            180                 185                 190

Ser Phe Thr Asp Tyr Arg Leu Ile Ser Cys Asn Thr Ser Val Ile Thr
        195                 200                 205

Gln Ala Cys Pro Lys Val Thr Phe Glu Pro Ile Pro Ile His Tyr Cys
    210                 215                 220

Ala Pro Ala Gly Phe Ala Leu Leu Lys Cys Lys Asp Lys Lys Phe Asn
225                 230                 235                 240

Gly Thr Gly Pro Cys Lys Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Val Val Ile Arg Ser Glu Asn Phe Ser Asn Asn Ala Arg
        275                 280                 285

Thr Ile Ile Val Gln Leu Asn Thr Ser Val Glu Ile Lys Cys Ile Arg
    290                 295                 300

Pro Asn Asn Asn Thr Arg Lys Gly Ile His Ile Gly Pro Gly Arg Ala
```

-continued

```
305                 310                 315                 320

Phe Tyr Thr Thr Gly Asp Ile Ile Gly Asp Ile Arg Gln Ala His Cys
                325                 330                 335

Asn Ile Ser Arg Gln Asn Trp Asn Asn Thr Leu Lys Gln Ile Ala Glu
            340                 345                 350

Lys Leu Arg Glu Gln Phe Gly Asn Lys Thr Ile Val Phe Arg Asn Ser
        355                 360                 365

Ser Gly Gly Asp Pro Glu Ile Val Met His Thr Phe Asn Cys Ala Gly
    370                 375                 380

Glu Phe Phe Tyr Cys Asn Thr Ala Glu Leu Phe Asn Ser Thr Trp Tyr
385                 390                 395                 400

Ala Asn Gly Thr Ile Ser Ile Gly Gly Gly Asn Lys Thr Asn Ile Ile
                405                 410                 415

Leu Pro Cys Arg Ile Lys Gln Phe Ile Asn Met Trp Gln Glu Val Gly
            420                 425                 430

Lys Ala Met Tyr Ala Pro Pro Ile Ser Gly Gln Ile Arg Cys Ser Ser
        435                 440                 445

Asn Ile Thr Gly Leu Leu Leu Thr Arg Asp Gly Gly Arg Gly Asn Gln
    450                 455                 460

Thr Asp Asn Gln Thr Glu Ile Phe Arg Pro Val Gly Gly Asp Met Lys
465                 470                 475                 480

Asn Asn Trp Arg Ser Glu Leu Tyr Lys Tyr Lys Val Val Arg Ile Glu
                485                 490                 495

Pro Leu Gly Ile Ala Pro Thr Arg Ala Lys Arg Arg Val Val Gln Arg
            500                 505                 510

Glu Lys Arg Ala Val Gly Ile Gly Ala Leu Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Leu Leu Leu Ser Gly Ile Val Gln Gln Gln Asn Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Gly Lys Leu Ile Cys
        595                 600                 605

Thr Thr Ala Val Pro Trp Asn Val Ser Trp Asn Asn Arg Ser Val Asp
    610                 615                 620

Asp Ile Trp Glu Asn Met Thr Trp Met Gln Trp Asp Arg Glu Ile Ser
625                 630                 635                 640

Asn Tyr Thr Ser Leu Ile Tyr Thr Leu Ile Glu Glu Ser Gln Asn Gln
                645                 650                 655

Gln Glu Lys Asn Glu Gln Glu Leu Leu Ala Leu Asp Lys Trp Ala Asn
            660                 665                 670

Leu Trp Asn Trp Phe Asn Ile Thr Glu Trp Leu Trp Tyr Ile Lys Ile
        675                 680                 685

Phe Ile Met Ile Val Gly Gly Leu Val Gly Leu Arg Ile Val Phe Ala
    690                 695                 700

Val Leu Ser Ile Val Asn Arg Val Arg Gln Gly Tyr Ser Pro Leu Ser
705                 710                 715                 720

Phe Gln Thr His Leu Pro Ala Gln Arg Gly Pro Asp Arg Pro Gly Gly
                725                 730                 735
```

-continued

```
Ile Glu Glu Glu Gly Gly Glu Ser Asp Arg Asp Arg Ser Gly Arg Leu
            740                 745                 750

Val Asn Gly Phe Leu Ala Ile Ile Trp Ile Asp Leu Arg Ser Leu Cys
        755                 760                 765

Leu Phe Ser Tyr His His Leu Arg Asp Leu Leu Leu Ile Val Thr Arg
    770                 775                 780

Ile Val Glu Ile Leu Gly Arg Arg Gly Trp Glu Ile Leu Lys Tyr Trp
785                 790                 795                 800

Trp Asn Leu Leu Gln Tyr Trp Ile Gln Glu Leu Lys Asn Ser Ala Val
                805                 810                 815

Ser Leu Leu Asn Ala Ile Ala Ile Ala Val Gly Glu Gly Thr Asp Arg
            820                 825                 830

Ile Ile Glu Ala Phe Arg Ser Ile Phe Arg Ala Ile Leu His Ile Pro
        835                 840                 845

Thr Arg Ile Arg Gln Gly Leu Glu Arg Ser Leu Leu
    850                 855                 860
```

RAPID SELECTION METHOD FOR HIV GP-120 VARIANTS

CROSS-REFERENCE TO RELATED APPLICATIONS

This application is filed under the provisions of 35 U.S.C. §371 and claims the priority of International Patent Application No. PCT/EP2012/053185 filed on Feb. 24, 2012, of U.S. Provisional Patent Application No. 61/446,595 filed on Feb. 25, 2011, and of European Patent Application No. 11382051.8 filed on Feb. 25, 2011.

FIELD OF THE INVENTION

The present invention relates to a method for the rapid selection of immunogens that can elicit high neutralizing antibody (nAb) activities. Several examples of these immunogens with enhanced nAb activities are disclosed and exemplified. In particular, immunogens with increased antibody affinity against HIV-1 Env epitopes are disclosed.

BACKGROUND OF THE INVENTION

It is estimated that more than 60 million people worldwide have been infected by the human immunodeficiency virus since 1982. Nearly half of these infected individuals have died of the resultant Acquired Immunodeficiency Syndrome (AIDS) during the same time frame. Although the virus spread seems to have reached a plateau lately, 2.5 million HIV new infections were reported in 2009. HIV still is a major public health problem. See UNAIDS, 2010 Report on the global AIDS epidemic.

HIV-1 is one of the most genetically diverse viral pathogens described so far. There are three main branches of the HIV-1 phylogenetic tree, the M (main), N (new), and O (outlier) groups. Group M viruses are the most widespread, accounting for more than 99% of global infections. This group is presently divided into nine distinct genetic subtypes, or clades (A through K), based mostly on short env (envelope) gene sequences. See McCutchan F, AIDS 2000; 14(S3):S31-S44 and Robertson D, et al., Science 2000; 288:55-56.

Env is the most variable HIV-1 gene, with up to 35% sequence diversity between clades, 20% sequence diversity within clades, and up to 10% sequence diversity in a single infected person. See Kuiken C, et al., AIDS 1996; 10:31-37 and Shankarappa R, et al., J. Virol. 1999; 73:10489-10502. Clade B is dominant in Europe, the Americas, and Australia. See Kuiken C, et al., AIDS 1996; Am. J. Epidemiol. 2000; 152:814-822. Clade C is common in southern Africa, China, and India and presently infects more people worldwide than any other clade. See McCutchan, 2000, supra. Clades A and D are prominent in central and eastern Africa.

However, many viruses are difficult to classify into clades due to the common intermixing of co-circulating viruses that leads to interclade recombinants. See Heyndrickx L, et al., J. Virol. 200; 74:363-370 and McCutchan F, et al., Virology 1999; 254:226-234. Some recombinant forms have in fact given rise to important epidemic lineages, called circulating recombinant forms (CRFs). The two most common of these are CRF01 (AE), discovered in Thailand, which was initially classified as clade E, though later it was found to be clade E only in env and clade A in other parts of the genome, and CRF02, an AG recombinant form common in Western Africa. See Robertson, 2000, supra. Globally, clades A through D and the CRF01 AE and CRF02 AG recombinants account for more than 90% of global infections.

Neutralizing antibodies (nAbs) against viral envelope proteins (Env) are a first line of adaptive immune defense against HIV-1 exposure by blocking the infection of susceptible cells. See Kwong P, et al., Nature 1998; 393:648-659, Moore J, et al., J. Virol. 1994; 68:469-484, Moore P, et al., J. Virol. 1996; 70:1863-1872, and Parren P, et al., AIDS 1999; 13:S137-S162. The efficacy of vaccines against several viruses has been attributed to their ability to elicit nAbs. See Burton D, Nat. Rev. Immunol. 2002; 2: 706-713 and Zinkerangel R, et al., Adv. Immunol. 2001; 79:1-53. However, there has been limited progress towards the development of effective HIV-1 immunogens despite enormous efforts. See Burton, 2002, supra, McMichael A, Hanke T, Nat. Med. 2003; 9:874-880, and Moore, 1996, supra. The design of these immunogens requires the identification of epitopes capable of inducing better nAb responses. Unfortunately, all attempts to develop immunogens that elicit broadly nAbs responses have failed to the present.

Thus, there is a need in the art for new HIV-1 immunogens capable of inducing better nAb responses.

SUMMARY OF THE INVENTION

The present invention refers to a method for the rapid selection of immunogens (RIS) that can elicit high nAb activities when used as B cell immunogens. The method comprises: i) mutating randomly the nucleotide coding sequence of a wild type epitope of interest to generate a library of variants of said epitope, ii) testing the library with an antibody, or parts thereof, known to have affinity towards the wild type epitope, and iii) selecting the epitope variants that increases the affinity of the antibody. Preferably, the epitope is a HIV epitope. More preferably, the epitope is an Env epitope.

In a second embodiment, the invention relates to nucleotide sequences and peptides obtained by the RIS method such as the nucleotide sequences of SEQ ID NO:1 and SEQ ID NO:3.

In a third embodiment, the invention relates to the use of the nucleotide sequences and peptides obtained by the RIS method for the prevention and treatment of the diseases induced wholly or in part by the action of the wild type epitope of interest. Preferably, the disease is AIDS or a disease caused by an HIV infection.

In a fourth embodiment, the invention relates to the diagnostic use of the RIS method.

BRIEF DESCRIPTION OF THE FIGURES

FIG. 1. Sequence of the mutants identified using the MS method of the invention. The uppermost sequence corresponds to amino acids 121 to 160 of the AC10 gp160 polypeptide. The sequences of the corresponding regions in the isolated clones are shown as dots wherein the amino acid is the same as in the AC10 gp160 or with the corresponding amino acid in those positions wherein the sequence of the mutant differs from that of the wild-type.

FIG. 5. Alignment of SEQ ID NO:31 to the AC10 wild-type HXB2 sequence. The SEQ ID NO:31 has affinity towards the PG16 antibody. The modified sequence shows two mutations: i) N203S, in a potential glycosylation site and ii) G604E, in the gp41 immunodominant region.

DETAILED DESCRIPTION OF THE INVENTION

A. Rapid Immunogen Selection (RIS) Method

Figure 2:
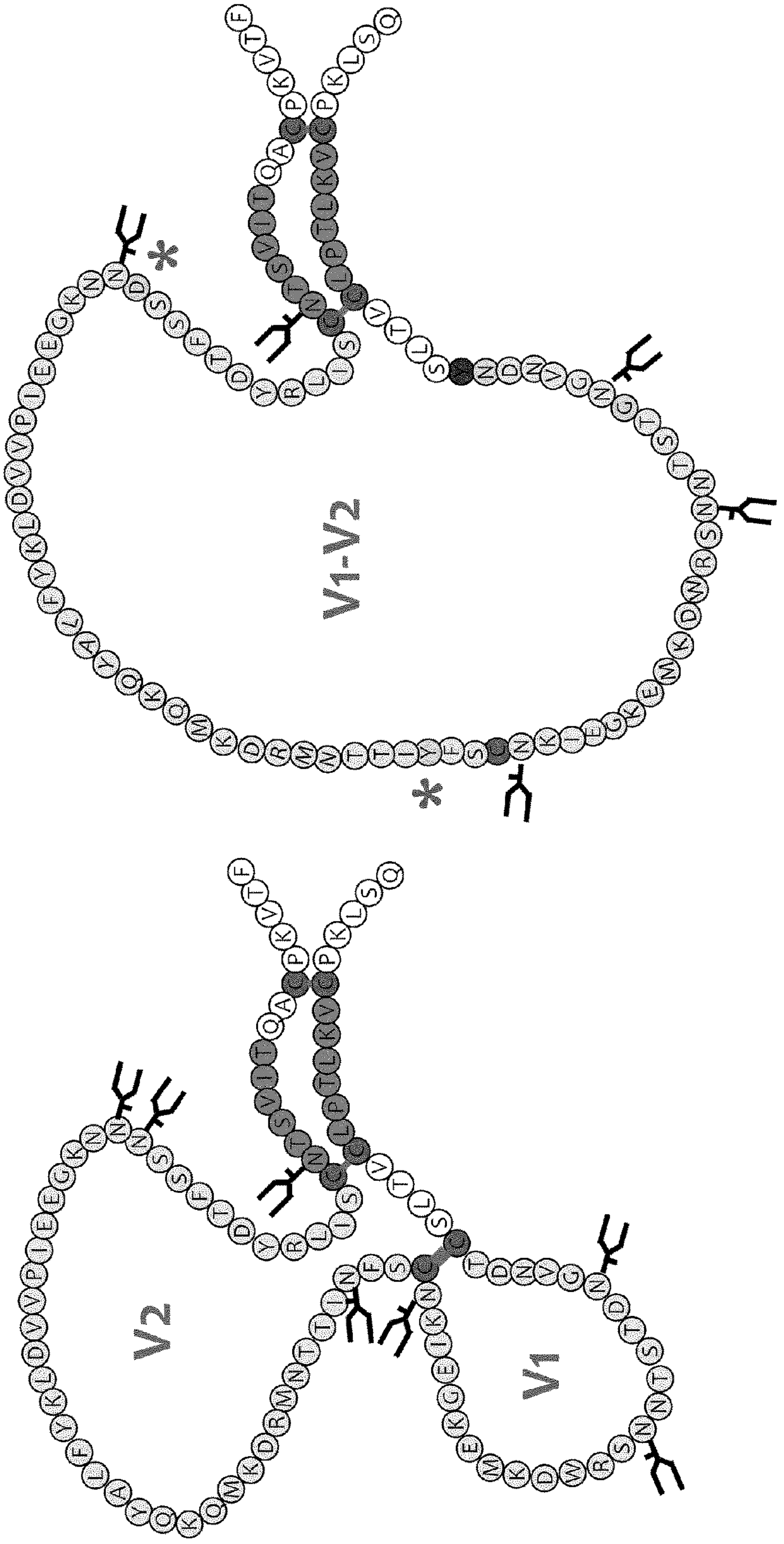
FIG. 2. Proposed interaction between the 4E10 antibody and LR1-C1 specific mutant. Eleven amino acid substitutions across the entire env gene are shown, including the loss of 3 potential N-linked glycosylation sites. The C131Y mutation is especially relevant because this substitution eliminates the native disulfide bond between C131 and C157 disrupting the architecture of the V1/V2 loop.
Figure 3:
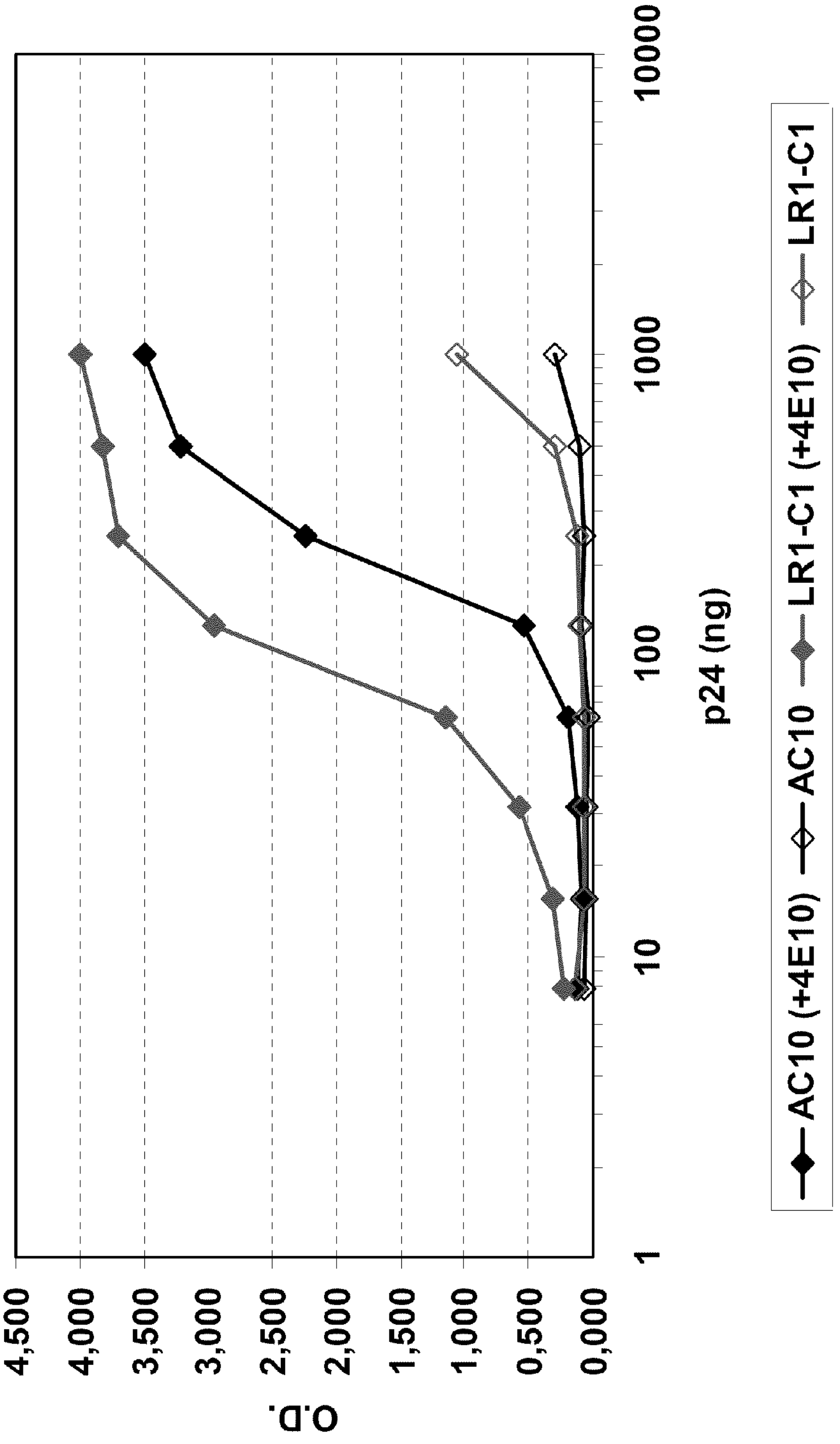
FIG. 3. The LR1-C1 virion identified using the MS method according to the invention shows increased affinity towards the broadly neutralizing antibody 4E10. The graph shows a titration of the binding of virions to plates coated with the 4E10 antibody as determined by adding increasing amount of the AC10 wild-type isolate and the LR1-C1 isolate to plates either coated with the 4E10 antibody or left untreated. The diagram illustrates a 4-fold increase in the affinity of the 4E10 antibody to the LR1-C1 in comparison to the wild-type variant.
Figure 4:
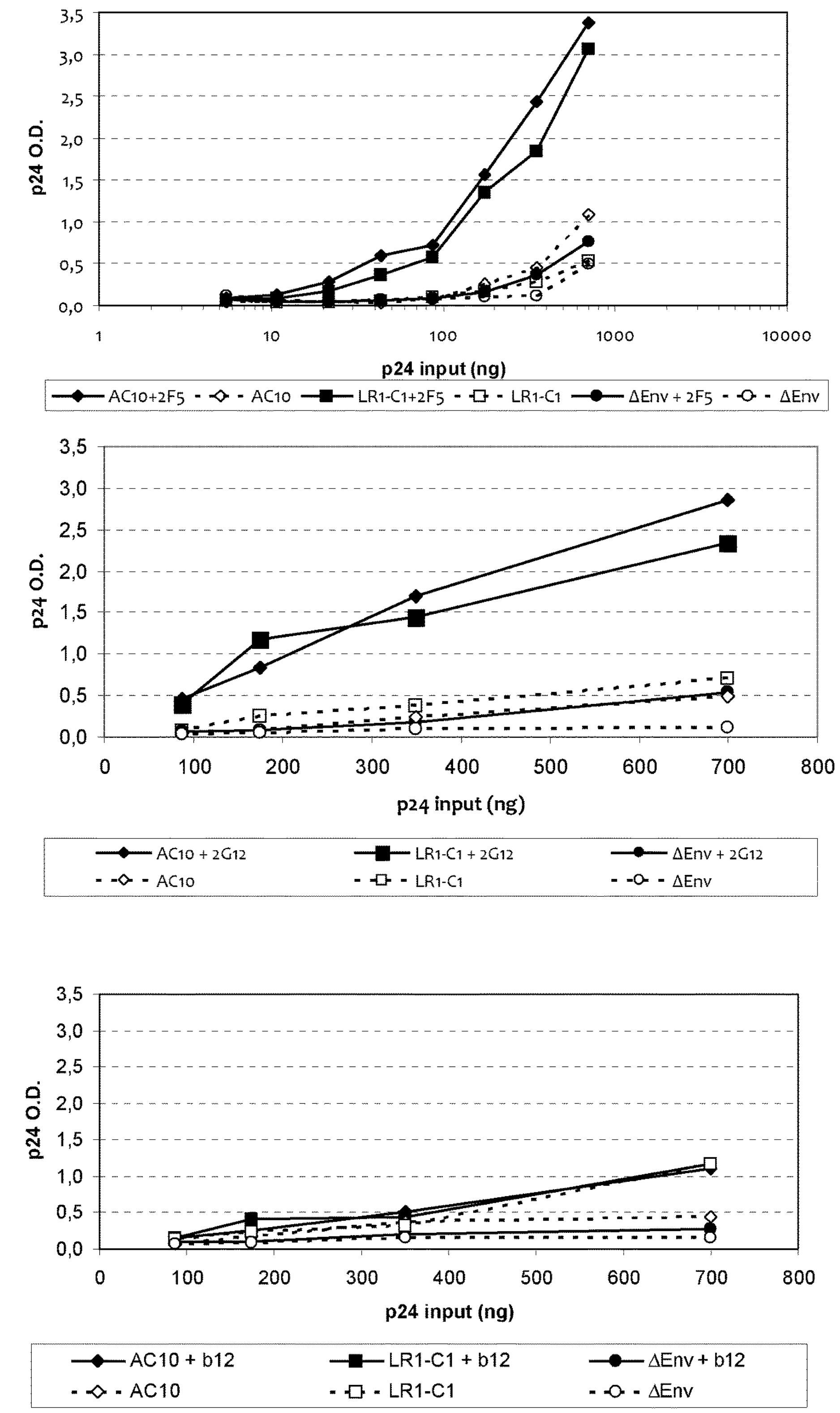
FIG. 4. The LR1-C1 virion identified using the RIS method according to the invention with the 4E10 antibody does not show increased affinity towards other broadly neutralizing antibodies. The graph shows a titration of the binding of virions to plates coated with the 2F5 (panel A), 2G12 (panel B) or b12 (panel C) antibodies as determined by adding increasing amount of the AC10 wild-type isolate, the LR1-C1 isolate or virions carrying a deletion in the env gene to plates either coated with the antibodies or left untreated.

The invention refers to a new approach for optimizing the HIV-1 envelope protein (Env) as an immunogen. This approach takes into account that the ability of an epitope to elicit antibodies depend on its exposure on the virion. The method is based on the selection of variants with increased affinity for broadly nAbs from a library of virions with randomly mutated envelope proteins.

According to the invention, the full-length env gene from HIV strain AC10 is used to generate libraries of randomly mutated envelopes by a PCR-based method. Cloning was performed into pNL4-3 context and virions were obtained by transient transfection into 293T cells. Selection of viruses with increased affinity to the broadly nAb 4E10 was carried out by an improved in-solution virion capture assay. RNA was extracted from the captured virus population and reverse transcription PCR was performed to obtain the env gene from the corresponding viruses for further sequencing and cloning back into pNL4-3 context. After one round of selection, an envelope with a 4-fold increase in affinity to 4E10 antibody was isolated. See examples.

Thus, in a first aspect, the invention relates to a method for the identification of immunogens capable of eliciting neutralizing antibodies against a polypeptide which comprises:

(i) contacting a neutralizing antibody specific for said polypeptide with a library of recombinant viruses, each of said recombinant viruses containing a randomized gene encoding a variant of said polypeptide and expressing said polypeptide, (ii) separating those members of the library of recombinant viruses that bind to the neutralizing antibody from members that do not so bind on the basis of their ability to bind to the neutralizing antibody, and (iii) determining the sequence of the variant polypeptides found in the members of the library of recombinant viruses selected in step (ii).

The term "immunogen" as used herein, is intended to denote a substance of matter, which is capable of inducing an adaptive immune response in an individual, where said adaptive immune response is capable of inducing an immune response, which significantly engages pathogenic agents, which share immunological features with the immunogen.

The term "eliciting" when referred to an immune response, as used in the present invention, refers to specifically controlling or influencing the activity of the immune response, and includes activating an immune response, up-regulating an immune response, enhancing an immune response and/or altering an immune response (such as by eliciting a type of immune response which in turn changes the prevalent type of immune response in a subject from one which is harmful or ineffective to one which is beneficial or protective).

The term "neutralizing antibody" is any antibody or antigen-binding fragment thereof that binds to a pathogen and interferes with the ability of the pathogen to infect a cell and/or cause disease in a subject. Typically, the neutralizing antibodies used in the method of the present invention bind to the surface of the pathogen and inhibit or reduce infection by the pathogen by at least 99 percent, at least 95 percent, at least 90 percent, at least 85 percent, at least 80 percent, at least 75 percent, at least 70 percent, at least 60 percent, at least 50 percent, at least 45 percent, at least 40 percent, at least 35 percent, at least 30 percent, at least 25 percent, at least 20 percent, or at least 10 percent relative to infection by the pathogen in the absence of said antibody(ies) or in the presence of a negative control. The nAbs can then be tested to determine if they have a neutralizing activity or BNAb activity using any of the methods provided herein. If the neutralizing antibodies or BNAbs were raised in a non-human animal, the CDRs can be transferred from the non-human framework to a human framework to generate an antibody suitable for administration to a human. Methods for determining whether an antibody is a nAb have been described in the art. See Li M, et al., J. Virol. 2005; 79:10108-10125, Wei X, et al., Nature 2003; 422:307-312, and Montefiori D, Curr. Protoc. Immunol. 2005; January, Chapter 12:Unit 12.11. These methods are based on the determination of the reduction in expression of a reporter gene after a single round of viral infection using a receptive cell line using a virus which encodes the reporter gene.

The term "virus", as used herein, refers to a small infectious agent that can replicate only inside the living cells of organisms. Non-limiting examples of viral families that may be used in the method of the present invention include adenoviridae, African swine fever-like viruses, arenaviridae, arterivirus, astroviridae, baculoviridae, birnaviridae, bunyaviridae, caliciviridae, circoviridae, coronaviridae, deltavirus, filoviridae, flaviviridae, hepadnaviridae, hepeviridae, herpesviridae, orthomyxoviridae, paramyxoviridae, picomaviridae, poxyviridae, reoviridae, retroviridae and rhabdoviridae.

A.1 Contacting Step

In a first step, the method of the invention involves contacting a neutralizing antibody specific for a polypeptide displayed on the surface of said virus with a library of recombinant viruses, each of said recombinant viruses containing a randomized gene encoding a variant of said polypeptide displayed on the surface of the virus.

The term "library", as used herein, refers to a diverse collection or mixture of polynucleotides comprising polynucleotides encoding different recombinant polypeptides. The size and complexity of the libraries to be used in the methods of the present invention may be varied. For example, the methods of the invention can be used to screen libraries with up to 500000 different members, or libraries with $1\times10^6$, $1\times10^8$ or more members. Typical virus libraries have $1\times10^8$ to $1\times10^{13}$ members, and such libraries can be screened using the methods of the invention. Indeed, such libraries are preferred, although the methods can clearly also be used for screening much smaller libraries (e.g. libraries with 1000 to 50,000, 50 to 1000, or 100 to 500, or 10 to 100, or 5 to 100 members). Diversity in the variant library can be generated via mutagenesis of the genes encoding the variants at the DNA triplet level, such that individual codons are variegated (e.g. by using primers of partially randomized sequence in a PCR reaction).

When libraries of molecules are referred to herein, the term can be used to refer to such a library at the nucleic acid or protein level (i.e. before or after expression of the encoded proteins has taken place). Clearly, however, such expression libraries must be present at the protein level in order for the selection of interacting binding partners to take place. Thus, in order for the contacting step (a) to successfully occur, the libraries have to be present at the protein level (although initially they may be present at the nucleic acid level).

In a preferred embodiment, the polypeptide against which neutralizing antibodies are used in step (i) are expressed in the virus. In a preferred embodiment, the polypeptide is displayed "on the surface of a virus". As used herein this term refers to any polypeptide that is accessible to reagents, such as antibodies, without the need of disrupting the virus structure. It will be understood that the polypeptide displayed on the surface may be a capsid polypeptide for not-enveloped viruses or an envelope polypeptide for enveloped viruses. In a preferred embodiment, the polypeptide displayed on the surface of a virus is an envelope polypeptide.

Any viral envelope protein may be engineered in order to obtain a library of recombinant viruses, each of said recombinant viruses containing a randomized gene encoding a variant of said polypeptide. Illustrative antigens include those selected from influenza virus haemagglutinin, human respiratory syncytial virus G glycoprotein, core protein, matrix protein or other protein of Dengue virus, measles virus haemagglutinin, herpes simplex virus type 2 glycoprotein gB, poliovirus I VP1, envelope or capsid glycoproteins of HIV-1 or HIV-II, hepatitis B surface antigen, diptheria toxin, streptococcus 24M epitope, gonococcal pilin, pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulinahydodysenteriae protective antigen, bovine viral diarrhea glycoprotein 55, Newcastle disease virus hemagglutinin-neuraminidase, swine flu hemagglutinin, swine flu neuraminidase, foot and mouth disease virus, hog colera virus, swine influenza virus, African swine fever virus, mycoplasma liyopneutiioniae, infectious bovine rhinotracheitis virus, infectious bovine rhinotracheitis virus glycoprotein E, glycoprotein G, infectious laryngotracheitis virus, infectious laryngotracheitis virus glycoprotein G or glycoprotein I, a glycoprotein of La Crosse virus, neonatal calf diarrhoea virus, Venezuelan equine encephalomyelitis virus, punta toro virus, murine leukemia virus, mouse mammary tumor virus, hepatitis B virus core protein and hepatitis B virus surface antigen or a fragment or derivative thereof, antigen of equine influenza virus or equine herpes virus, including equine influenza virus type A/Alaska 91 neuraminidase, equine influenza virus typeA/Miami 63 neuraminidase, equine influenza virus type A/Kentucky 81 neuraminidase equine herpes virus type 1 glycoprotein B, and equine herpes virus type 1 glycoprotein D, antigen of bovine respiratory syncytial virus or bovine parainfluenza virus, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhea virus glycoprotein 48, and glycoprotein 53.

Preferably, the library of recombinant viruses is a library of retrovirus. The term "retrovirus" means any RNA virus that is replicated in a host cell via the enzyme reverse transcriptase to produce DNA from its RNA genome and that belongs to the family retroviridae.

The term "retrovirus" is used herein in its conventional meaning and generally encompasses a class of viruses in which the genetic material is single-stranded RNA and which employ reverse transcriptase to transcribe the viral RNA into DNA in a host Retroviruses as intended herein may particularly belong to the viral family retroviridae, more particularly to sub-families oncovirinae, lentivirinae or spumavirinae retroviruses as intended herein may be pathogenic. Env sequences can be derived from any known retrovirus, including but not limited to HIV, MuLV, SMRV, SFV, HPV, MMTV, SRVs, HTLV-I, HTLV-II, BLV, BIV, SIV, visna virus, EIAV, FIV, and EIAV, and from any of the retroviral subfamilies (e.g. oncovirinae, lentivirinae, or spumavirinae). Many retroviral clones, including HIV-1 clones, are well characterized and available.

Particularly intended herein are retroviruses infecting animals, more preferably retroviruses of warm-blooded animals, even more preferably of vertebrate animals, still more preferably of mammals, yet more preferably of primates, and most preferably of humans. Particularly preferred herein are human retroviruses including without limitation HIV-1, HIV-2, HTLV-I and HTLV-2. Well-established repositories of HIV (and other retroviral) sequence information include GenBank, EMBL, DDBJ and the NCBI. Well characterized HIV-1 clones include HXCB2, HIV-1-MN and HIV-1-MN-ST.1. See Hall L, et al., J. Virol. 1992; 66(9):5553-5560.

In a preferred embodiment, the library of recombinant viruses is a library of HIV viruses resulting from the randomization of at least one surface polypeptide. The acronym "HIV" is used herein to refer to human immunodeficiency viruses generically and includes all clades and/or strains of human immunodeficiency virus 1 (HIV-1) and human immunodeficiency virus 2 (HIV-2) and is synonymous with the older terms for HIV, such as HTLVIII and LAV.

In a still more preferred embodiment, the different members of the HIV library are randomized in the env gene. As used herein, the term env gene indicates the polynucleotide of the viral genome that encodes the envelope protein of HIV. As used herein, the terms "Env polypeptide" or "envelope polypeptide" refers to a molecule derived from an HIV envelope protein. The envelope protein of HIV is a glycoprotein of about 160 kd (gp160). During virus infection of the host cell, gp160 is cleaved by host cell proteases to form gp120 and the integral membrane protein, gp41.

A "gp120 polypeptide" is a molecule derived from a gp120 region of an Env polypeptide. The mature gp120 wild-type polypeptides have about 500 amino acids in their primary sequence. Gp120 is heavily N-glycosylated giving rise to an apparent molecular weight of 120 kD. The amino acid sequence of gp120 is approximately 511 amino acids. Gp120 contains five relatively conserved domains (C1-C5)

interspersed with five variable domains (V1-V5). The variable domains contain extensive amino acid substitutions, insertions and deletions. A "gp120 polypeptide" includes both single subunits and multimers. The gp41 portion is anchored in (and spans) the membrane bilayer of the virion, while the gp120 segment protrudes into the surrounding environment. The receptor binding domain of gp120 is localized to N-terminal half of the protein. This is followed by a proline rich region (PRR), which is proposed to behave either as a hinge or trigger to communicate receptor binding to the fusion machinery. The C-terminus of the gp120 is highly conserved and interacts with the gp41. Exemplary sequences of wt gp160 polypeptides are available. See GenBank accession nos. AAB05604 and AAD12142.

The randomization of the env gene can be carried out over the complete env gene sequence or, preferably, over the part of the env gene that corresponds to the coding region for gp120, since this is the molecule which interacts with the receptor on the target cell and which constitutes the best candidate for binding to the neutralizing antibodies. Moreover, the randomization of the region of the env gene encoding gp120 can be carried out over the complete sequence or directed to one or more of the domains of the gp120 polypeptide. Thus, the RIS method according to invention contemplates the use HIV libraries resulting from the randomization in any of the conserved loops (C1 to C5) of gp120, in any of the variable loops (V1-V5) in gp120 or in a preferred combination of conserved regions and variable loops. In a preferred embodiment, the randomization is carried out over the whole env gene. In another embodiment, the randomization is carried out in the region of the env gene corresponding to gp120. In another embodiment, the randomization is carried out in the regions of the env gene corresponding to the V1 and/or V2 regions of gp120.

Any mutagenesis techniques can be used to introduce the mutation in the nucleic acid molecule. See Sambrook J, et al., "Molecular Cloning. A Laboratory Manual" (Cold Spring Harbor Laboratory Press, Cold Spring Harbor, N.Y., US, 1989), Bishop T, et al., "Nucleic Acid and Protein Sequence. A Practical Approach" (IRL Press, Oxford, England, 1987), Reznikoff W, Ed., "Maximizing Gene Expression" (Butterworths Publishers, Stoneham, Mass., US, 1987), Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, Germany 2001), Adereth Y, et al., Biotechniques 2005, 38:864-868, Allan J, et al., Biotechniques 1995; 18:746-750, Bubeck A, et al., J. Virol. 2004, 78:8026-8035, Doran B, US Pat. Pub. 20070111201, Locher C, et al., DNA Cell Biol. 2005; 24:256-263, Vasl J, et al., Biotechniques 2004; 37:726-730, Weiss G, et al., Proc. Natl. Acad. Sci. USA 2000; 97:8950-8954, and Delcourt M, U.S. Pat. No. 6,924,112. Mutagenesis strategies include random mutagenesis, Ala-scan mutagenesis, site-specific mutagenesis, and chimeric recombination. Mutagenesis kits and services are widely available commercially.

The term "neutralizing antibodies" includes the subclass of BNAbs. As used herein, "broadly neutralizing antibody" or "BNAb" is understood as an antibody obtained by any method that when delivered at an effective dose can be used as a therapeutic agent for the prevention or treatment of HIV infection or AIDS against more than 7 strains of HIV, preferably more than 8, 9, 10, 11, 12, 13, 14, 15, 16, 17, 18, 19, 20, or more strains of HIV. Suitable neutralizing antibodies for use in the RIS method according to the present invention include, without limitation, antibodies directed against the membrane-proximal external region (MPER), antibodies directed against the CD4 binding site and antibodies directed against the high-mannose glycans. In preferred embodiments, the neutralizing antibodies for use in the RIS method according to the present invention include one or more of an antibody selected from the group consisting of:

a) the 4E10 antibody which recognizes a segment of the gp41 ectodomain adjacent to the viral membrane. See Cardoso R, et al., *Immunity* 2005; 22:163-173, PHSL accession number 90.091703, NIH ARRRP catalog number 10091, and Katinger H, et al., U.S. Pat. No. 5,753,503;
b) the 2F5 antibody which recognizes a segment of the gp41 ectodomain adjacent to the viral membrane. See Ofek G, et al., J. Virol. 2004; 78:10724-10737, PHSL accession number 90.091704, NIH ARRRP catalog number 1475, and Katinger, supra;
c) the antibodies described in EP 0822941 binding to two different antigenic determinants of HIV-1, wherein the antigenic determinants are fragments of gp160 and correspond to amino acid sequences 79 to 184 and 326 to 400 of processed gp120 of HIV-1 isolate BH 10. See PHSL accession numbers 95032240 and 95032241;
d) The 2G12 which recognizes carbohydrates on the outer gp120 surface (mAb 2G12). See Trkola A, et al., J. Virol. 1996; 70:1100-1108, EACC accession number 93091517, and NIH ARRRP catalog number 1476;
e) the b12 antibody which recognizes the CD4 binding site. See Burton D, et al., Science 1994; 266: 1024-1027, NIH ARRRP catalog number 2640 and Burton D, et al., EP 0675904; and
f) the neutralizing antibodies PG9, PG16, PG20, PGG14, and PGC14. See Chan-Hui P, et al., WO2010107939.

Methods for determining whether an antibody is a nAb have been described in the art. Some of these methods are based on the determination of the reduction in effect of the antibody of the expression of a reporter gene after a single round of viral infection using a receptive cell line that encodes the reporter gene. See Li, 2005, Wei, 2003, Montefiori, 2005, supra, and Alvin C, WO2009117661.

The neutralizing capacity of the antibodies for use according to the present invention may be characterized by the IC50 (i.e. the concentration of antibody which causes a 50% reduction in the infection of a target cell). Preferably, neutralizing antibodies for use according to the present invention have an IC50 of 2 μg/ml or lower (less than 0.15 μg/mL, less than 0.125 μg/mL, less than 0.10 μg/mL, less than 0.075 μg/mL, less than 0.05 μg/mL, less than 0.025 μg/mL, less than 0.02 μg/mL, less than 0.015 μg/mL, less than 0.0125 μg/mL, less than 0.01 μg/mL, less than 0.0075 μg/mL, less than 0.005 μg/mL or less than 0.004 μg/mL (an antibody concentration of $10^{-8}$ or lower, preferably $10^{-9}$ M or lower, preferably $10^{-10}$ M or lower, i.e. $10^{-11}$ M, $10^{-12}$ M, $10^{-13}$ M or lower). This means that only very low concentrations of antibody are required for 50 percent neutralization of a clinical isolate of HIV in vitro. Potency can be measured using a standard neutralization assay as described in the art.

The contacting step is carried out under conditions adequate so that those members of the library of recombinant viruses capable of specifically binding to the neutralizing antibodies actually bind to said antibodies.

As used herein, the term "specifically bind" (or derivatives thereof), refers to the interaction between binding pairs (e.g. two proteins or compounds). In some embodiments, the interaction has an affinity constant of at most $10^{-6}$ moles/ liter, at most $10^{-7}$ moles/liter, or at most $10^{-8}$ moles/liter. In general, the phrase "specifically binds" refers to the specific binding of one compound to another, wherein the level of binding, as measured by any standard assay (e.g. an immunoassay), is statistically significantly higher than the background control for the assay.

The conditions during the contacting step can be determined in a routine manner by the skilled artisan. Exemplary "contacting" conditions may comprise incubation for 15 minutes to 4 hours (e.g. one hour, at 4° C., 37° C. or at room temperature). However, these may be varied as appropriate according to, for example, the nature of the interacting binding partners. The sample may optionally and preferably be subjected to gentle rocking, mixing or rotation. In addition, other appropriate reagents such as blocking agents to reduce non specific binding may be added. For example, 1-4 percent BSA or other suitable blocking agent (e.g. milk) may be used. It will be appreciated however that the contacting conditions can be varied and adapted by a skilled person depending on the aim of the screening method. For example, if the incubation temperature is, for example, room temperature or 37° C., this may increase the possibility of identifying binders which are stable under these conditions (e.g. in the case of incubation at 37° C., binders which are stable under conditions found in the human body). Such a property might be extremely advantageous if one or both of the binding partners was a candidate to be used in some sort of therapeutic application (e.g. an antibody). Such adaptations are within the ambit of the skilled person.

In a preferred embodiment, the neutralizing antibody used in the contacting step may be immobilized on a solid support using a variety of techniques known to those in the art, which are amply described in the patent and scientific literature. The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor. See Jorgenson R, et al., U.S. Pat. No. 5,359,681.

The antibody may be immobilized on the solid support using a variety of techniques known to those in the art, which are amply described in the patent and scientific literature. In the context of the present invention, immobilization includes both non-covalent association, such as adsorption, and covalent attachment (which may be a direct linkage between the antigen and functional groups on the support or may be a linkage by way of a cross linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In an embodiment, contacting a well of a plastic microtiter plate (such as polystyrene or polyvinylchloride) with an amount of antibody ranging from about 10 ng to about 1 and preferably about 100-200 ng, is sufficient to immobilize an adequate amount of polypeptide.

Covalent attachment of antibody to a solid support may also be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner, using well known techniques.

Alternatively, instead of immobilizing the neutralizing antibody to a support either covalently or non-covalently, the invention contemplates the possibility of immobilizing the antibody by binding to a first antibody specific for Fc or an anti-Fc antibody fragment; which has been previously immobilized to the support. In addition to helping capturing the antibody, the first antibody orients the neutralizing antibody to increase the percentage of immobilized antibody that is active for binding to the members of the viral library. For instance, the immobilization may be carried out by first contacting an antibody that has been immobilized on a solid support, commonly the well of a microtiter plate, with the library, such that those viruses within the library showing affinity towards the neutralizing antibody sample are allowed to bind to the immobilized antibody. The unbound sample is then removed from the immobilized antibody-virus complexes. More specifically, once the antibody is immobilized on the support as described above, the remaining protein binding sites on the support are typically blocked.

A.2 Separation Step

In a second step, the RIS method of the invention comprises separating those members of the library of recombinant viruses that bind to the neutralizing antibody from members that do not so bind on the basis of their ability to bind to the neutralizing antibody.

Said separation step can refer to a physical separation (e.g. on beads or FACS) or removal of the solid phase from the reaction mixture, or can refer to a step in which the solid phase is subjected to one or more washing steps in order to remove the other components of the reaction mixture. In embodiments where physical separation or removal of the solid phase is carried out, then, preferably, the solid phase is also subjected to one or more washing steps.

The washing steps may be carried out in any appropriate way depending on the nature of the solid phase and the interacting binding partners attached thereto. Appropriate methods of washing particulate solid phases are well known to a person skilled in the art. For example, if the solid phase is particulate, the washing steps may take place by centrifuging the particles under such conditions that they form a pellet while the supernatant is removed. Then, the particles may be re-suspended in an appropriate aqueous medium (e.g. the same medium utilized in the contacting step). The stringency of the washes (or indeed, the contacting step) can be modified by adding appropriate reagents well known to a person skilled in the art (e.g. Tween) in order to, for example, decrease background or unspecific binding. Such steps of pelleting and re-suspension would constitute one wash. Any appropriate number of washes could be carried out. If however, the solid phase was magnetic, then the wash steps could conveniently be carried out by applying a magnetic field to the vessel in which the contacting step had been carried out, removing the supernatant and re-suspending the solid phase in an appropriate aqueous medium. Such steps of magnetic separation and re-suspension would constitute one washing step and any appropriate number of washes could be carried out. If the solid support is non-particulate (e.g. is a planar surface such as a plate, a dish or a filter), then again appropriate methods of washing such solid phases are well known to a person skilled in the art.

As well as the above described optional washing steps, it should be noted that one or more washing steps can also be carried out at any other appropriate stage in the RIS method.

For example, one or more steps of washing the solid phases might also be carried out after any immobilization step has been performed, for instance, to remove neutralizing antibodies which have not become bound to the solid phase. Indeed, such washing steps are preferred. Also, one or more washing steps may be carried out on the solid phases at other appropriate times during the course of the method to remove, for example, non-bound entities. The number of washes required can be determined readily by a person skilled in the art.

Once the components of the reaction mixture which either bind weakly of bind non-specifically to the neutralizing antibodies are removed, the separation step is finally carried out by eluting those members of library of recombinant viruses which have bound specifically to the neutralizing antibodies. Depending on the type immobilization, said elution step could be carried out by any suitable method, such as, for example, by utilizing an alkaline, detergent or similar agent which breaks non-covalent bonds, followed by neutralization, to allow the interacting partners to refold and bind to each other. In the case of biotin tags, generally, the library constructs containing such tags are engineered to contain some kind of site for cleavage like a protease site, a restriction enzyme site, or a cleavable S-S linker moiety which can be opened with dithiotreitol (DTT). TEA might also be used. A cleavage site such as those described above can be used with any type of tag in order to enable or facilitate elution.

The release of the viruses from the neutralizing antibody as a result of the elution step can be carried out typically by measuring the presence of one or more virus polypeptides in the supernatant. In a preferred embodiment, the assayed polypeptide is a viral capsid polypeptide. When an HIV library is used particularly, non-limiting examples of HIV proteins that may be suitable for use in the embodiments presented herein include the HIV gag proteins p53, p24, p17, p'7, p6, p2 or p1, the HIV env glycoproteins gp120, gp41 or gp160, HIV enzymes including integrase (p31), reverse transcriptase (p51 or p66), RNase H (p15), protease (p10), the HIV nef proteins (p25/p27), the HIV vif protein p23, the HIV rev protein p19, the HIV vpr protein (p12/p10), HIV vpu protein (p16) or HIV tat proteins (p16/p14). In a preferred embodiment, the HIV polypeptide assayed to establish whether the selected virus has been effectively eluted from the neutralizing antibody is p24.

As used herein, the term "HIV p24" refers to the gene product of the gag region of HIV, characterized as having an apparent relative molecular weight of about 24,000 daltons. The term "HIV p24" also refers to modifications and fragments of p24 having the immunological activity of p24.

P24 can be measured with enzyme immunoassays whereas detection of bound p24 requires pretreatment with an acid to dissociate the complex. Although procedures vary between manufacturers, HIV p24 antigen tests employ ELISA technology with modifications to detect antigen, not antibody. In a representative assay, such as an "antibody sandwich" type, a specific monoclonal antibody to HIV p24 is attached to the solid phase (microtiter plate-well or polystyrene bead) acting to "capture" the viral antigen in the sample when added. A detergent (e.g. Triton X100) is added to disrupt virions and if antigen is present in the medium, the antigen will attach to the monoclonal antibody on the solid phase.

A.3 Detection Step

In a third step, the RIS method according to the invention comprises determining the sequence of said variant peptide displayed on the surface of the virus on those members of the library selected in step (ii).

Once one or more sets of interacting members of the viral libraries have been selected or isolated in accordance with the methods of the invention, these are subjected to further analysis. Said further analysis or uses generally require the candidate binding partners to be detached, removed, isolated or eluted from the neutralizing antibody and further expressed or produced. Thus, the method of the present invention further comprises a step wherein said members of the viral library capable of specifically interacting with the neutralizing antibody are detached, removed, eluted, or preferably isolated or are expressed or produced in isolation from each other. Said further analysis generally involves the isolation of individual interacting library members by isolation of the RNA from the bound viruses, reverse transcribing the viral RNA into cDNA and cloning said cDNA into a suitable expression vector.

Once the DNA encoding the binding partners are cloned in a suitable expression vector, the DNA encoding the binding partner can be sequenced or the protein can be expressed in a soluble form and subjected to appropriate binding studies to further characterize the candidates at the protein level. Appropriate binding studies will depend on the nature of the binding partners, and include, but are not limited to ELISA, filter screening assays, FACS or immunofluorescence assays, BiaCore affinity measurements or other methods to quantify binding constants, staining tissue slides or cells and other immunohistochemcal methods. Such methods are well established in the literature and one or more of them may be used to analyze the selected envelope protein variants.

As mentioned above, appropriate methods for analyzing the individual interacting binding partners are known in the art. One preferred method will be to sequence the genetic material of the viruses of the library which specifically bind to the neutralizing antibody.

Typically, in the case of retroviruses which have RNA as genetic material, the detection step involves the isolation of the RNA, reverse transcription of the RNA to yield single stranded cDNA, treating the single-stranded DNA to obtain double stranded DNA and cloning the double stranded cDNA in the vector of choice and sequencing the cDNA.

Reverse transcription is carried out using methods known to the skilled person and can be carried out isothermally, as well as by using thermostable RNA polymerases in the presence of a RNA-dependent DNA polymerase including, without limitation, AMV, Cloned AMV, MMLV, Superscriptll, ReverTraAce, Tth reverse transcriptase, hepatitis B reverse transcriptase, cauliflower mosaic virus reverse transcriptase, bacterial reverse transcriptase, and Thermoscript. The enzymes utilized in the present invention include those that have reduced, substantially reduced or completely eliminated RNase H activity. By an enzyme with "substantially reduced RNase H activity" is meant an enzyme that has less than about 20%, preferably less than about 15%, 10% or 5%, and most preferably less than about 2%, of the RNase H activity of the corresponding wild-type or RNase H+ enzyme, such as wild-type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of known assays. See Kotewicz M, et al., Nucl. Acids Res. 1988; 16:265-277, Gerard G, et al., Focus 1992; 14(5):91-93, and Kotewicz M, et al., U.S. Pat. No. 5,244,797. Particularly preferred polypeptides for use in the invention include, but are not limited to M-MLV reverse transcriptase, RSV reverse transcriptase, AMV reverse transcriptase, RAV (Rous-associated virus) reverse transcriptase, MAV (myeloblastosis-associated virus) reverse transcriptase, and HIV reverse transcriptase. See Kotewicz M, et al., U.S. Pat. No. 5,244,797, and Gerard G, et al., WO1998047912. It will be understood by one of ordinary skill, however, that any enzyme capable of producing a DNA molecule from a ribonucleic acid molecule (i.e. having reverse transcriptase activity) may be equivalently used in the compositions, methods and kits of the invention.

The single stranded cDNA can be treated so as to obtain a double-stranded DNA using any method known in the art. Preferably, the conversion of the single stranded cDNA to the double stranded DNA is carried out using in vitro amplification technologies such as Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA), linker-aided DNA amplification (LADA), Q-beta replicase amplification (Q-beta), loop-mediated isothermal amplification (LAMP) and Rolling Circle Amplification Technology (RCAT), or other in vitro enzymatic amplification technologies. The amplification step is carried out using primers corresponding to the sequences of the adapter regions. The resulting double-stranded DNA can be purified using a purification column, electromagnetic beads to which the primer is attached, or by electrophoresis through an agarose gel.

The resulting double stranded DNA can then be inserted into a vector of choice using methods known in the art. In a preferred embodiment, the primers used during the PCR-amplification step contain within their 5' regions target sites for restriction endonucleases which generate compatible ends with those present in the vector of choice. The endonuclease target sites allow the generation of cohesive ends that can be used for cloning the polynucleotides in appropriate vectors.

The sequencing step can be carried out using any known means of sequencing such as chemical sequencing (Maxam-Gilbert), Sanger dideoxy sequencing, pyrosequencing, fluorescence detection sequencing and mass spectrometry DNA Sequencing.

B. Immunogenic Polypeptides, Polynucleotides, Vectors and Host Cells

The rapid immunogen selection (RIS) method according to the present invention allows the identification of polypeptides which are variants of the polypeptide displayed on the surface of a virus and which are candidates for generating neutralizing antibodies and thus, for their use as immunogenic compositions or vaccines. Thus, in another aspect, the invention relates to polypeptides identified by the method of the invention.

The term "polypeptide", which is used interchangeably with protein herein, refers to a chain of amino acids of any length wherein the different amino acids are linked to one another by means of peptide bonds or disulphide bridges.

In the particular case wherein the virus selected according to the method of the invention is a retrovirus, then the polypeptide is a variant of an envelope protein. In a preferred embodiment, the retrovirus is HIV and the polypeptide according to the present invention is a gp120 variant.

The polypeptide identified according to the RIS method of the invention preferably comprises at least a mutation in a region selected from the group consisting of the C1 constant region, V1 variable region, V2 variable region, C2 constant region, C5 constant region and the gp41 ectodomain.

In a more preferred embodiment, the mutation in the C1 constant region is a mutation at position 88. In a more preferred embodiment, the mutated residue at position 88 is an Asp. In a still more preferred embodiment, the mutation in the C1 constant region is N88D mutation.

In a more preferred embodiment, the mutation in the V1 variable region is a mutation at one or more positions selected from the group consisting of positions 131, 132 and 138. In a more preferred embodiment, the mutated residues at positions 131, 132 and 138 in the V1 region are Y, N and/or G, respectively. In a still more preferred embodiment, the mutation in the V1 region is C131Y, T132N and/or D138G.

In a more preferred embodiment, the mutation in the V2 variable region is a mutation at one or more positions selected from the group consisting of positions 160 and 187. In a more preferred embodiment, the mutated residues in the V2 region are Y at position 160 and/or Asp at position 187. In a still more preferred embodiment, the mutation in the V2 region is N160Y and/or N191D.

In a more preferred embodiment, the mutation in the C2 constant region is a mutation at position 219. In a more preferred embodiment, the mutated residue at position 219 in the C2 region is Val. In a still more preferred embodiment, the mutation in the C2 region is I219V.

In a more preferred embodiment, the mutation in the C5 constant region is a mutation at one or more positions selected from the group consisting of positions 479 and 507. In a more preferred embodiment, the mutated residues at positions 479 and 507 in the C5 region are Ile and Trp, respectively. In a still more preferred embodiment, the mutation in the C5 region is M475I and/or R507W.

In a more preferred embodiment, the gp120 variant or fragment thereof according to the invention mutant carries the C131Y, T132N, D138G and N160Y mutations.

In a more preferred embodiment, the gp120 variant or fragment thereof according to the invention mutant carries the N88D, C131Y, T132N, D138G, N160Y, N191D, A225V, M479I, R507W and Y647N mutations.

In another embodiment, the gp120 variant or fragment thereof according to the invention carries the N203 S and G604E mutations.

In a more preferred embodiment, the mutation in the gp41 ectodomain is T643N.

The numbering of the positions mentioned above refers to the sequence of the gp160 preprotein encoded by the env gene (SEQ ID NO:1) of the HIV AC10HXb2 isolate depicted in SEQ ID NO:2, which is encoded by the env gene depicted in SEQ ID NO:1. See Li, 2005, supra and NCBI accession number AY835446.

In a preferred embodiment, the immunogenic polypeptide according to the invention comprises the env polypeptide of the LR1-C1 isolate (SEQ ID NO:4) encoded by the polynucleotide of SEQ ID NO:3 or a fragment thereof. The LR1-C1 isolate contains the N88D, C131Y, T132N, D138G, T132N, N160Y, N191D, A225V, M479I, R507W and Y647N mutations with respect to the numbering of SEQ ID NO:2.

In a preferred embodiment, the immunogenic polypeptide according to the invention comprises the env polypeptide of the clone 10 isolated with the PG16 antibody (SEQ ID NO:31) or a fragment thereof. The modified sequence shows the N203 S and G604E mutations.

In preferred embodiment, the immunogenic gp120 variant according to the invention or the fragment thereof comprises a sequence selected from the group consisting of SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:31.

Although the gp120 mutants showing increased affinity towards neutralizing antibodies have been determined in the present description have been derived from the AC10 HIV isolate (NCBI accession number AY835446 and env gene shown in SEQ ID NO:1), it will be appreciated that the immunogenic polypeptides according to the present invention may derive from other HIV isolates by replacing the corresponding positions in the env gene of said other HIV isolates. The corresponding positions in other HIV isolates can be determined without further ado using any suitable sequence alignment algorithm.

Methods of alignment of sequences for comparison are well known in the art. Optimal alignment of sequences for comparison can be conducted, for instance, by the Smith-Waterman local homology algorithm, by the Needleman-Wunsch homology alignment algorithm, by the Pearson-Lipman similarity search method, by computerized implementations of these algorithms or by manual alignment and visual inspection. See Smith T, Waterman M, Adv. Appl. Math. 1981; 2:482-489; Needleman S, Wunsch C, J. Mol. Biol. 1970; 48:443-453; Pearson W, Lipman D, Proc. Natl. Acad. Sci. USA 1988; 85:2444-2448; the GAP, BESTFIT, FASTA and TFASTA programs, Wisconsin Genetics Software Package, Genetics Computer Group, Madison, Wis., US; Ausubel F, et al., Eds, "Short Protocols in Molecular Biology", 4th Ed. (John Wiley and Sons, Inc., New York, N.Y., US).

A "fragment" is a unique portion of the polynucleotide encoding the HIV-1 envelope polypeptide of the present invention shorter in length than the parent sequence. Similarly, the term "fragment" refers to an HIV-1 envelope polypeptide of the present invention comprising up to the entire length of the defined peptide sequence minus one amino acid residue and the coding nucleotide sequence thereof. For example, a fragment may comprise from 5 to 2500 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250, 500 or at least 700 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25 percent or 50 percent) of a polypeptide as shown in a certain defined sequence. Clearly these lengths are exemplary, and any length that is supported by the specification, including the Sequence Listing, tables, and figures, may be encompassed by the present embodiments.

The present disclosure concerns nucleic acid constructs including polynucleotide sequences that encode antigenic gp120 polypeptides of HIV-1. These polynucleotides include DNA, cDNA and RNA sequences which encode the polypeptide of interest.

The term "polynucleotide", as used in this invention, refers to a polymer formed by a variable number of monomers wherein the monomers are nucleotides, including both ribonucleotides and deoxyribonucleotides. The polynucleotides include monomers modified by methylation as well as unmodified forms. The terms "polynucleotide" and "nucleic acid" are used interchangeably in this invention and include mRNA, cDNA and recombinant polynucleotides. As used in this invention, the polynucleotides are not limited to polynucleotides as they appear in nature, but include polynucleotides containing non-natural nucleotide analogues and internucleotide bonds.

Methods for the manipulation and insertion of the nucleic acids of this invention into vectors are well known in the art. See Sambrook, 1989, supra, and Ausubel F, et al., Eds., "Short Protocols in Molecular Biology", 4th Ed. (John Wiley and Sons, Inc., New York, N.Y., US, 2002).

Typically, the nucleic acid constructs encoding the gp120 polypeptides of the invention are plasmids. However, other vectors (e.g. viral vectors, phage, cosmids) can be utilized to replicate the nucleic acids. In the context of this invention, the nucleic acid constructs typically are expression vectors that contain a promoter sequence which facilitates the efficient transcription of the inserted genetic sequence. The expression vector typically contains an origin of replication, a promoter, as well as specific nucleic acid sequences that allow phenotypic selection of the transformed cells.

More generally, polynucleotide sequences encoding the gp120 polypeptides of this invention can be operably linked to any promoter and/or enhancer capable of driving expression of the nucleic acid following introduction into a host cell. A promoter is an array of nucleic acid control sequences that directs transcription of a nucleic acid. A promoter includes necessary nucleic acid sequences (which can be) near the start site of transcription, such as in the case of a polymerase II type promoter (a TATA element). A promoter also can include distal enhancer or repressor elements which can be located as much as several thousand base pairs from the start site of transcription. Both constitutive and inducible promoters are included. See Bitter G, et al., Meth. Enzymol. 1987; 153:516-544.

To produce such nucleic acid constructs, polynucleotide sequences encoding gp120 polypeptides are inserted into a suitable expression vector, such as a plasmid expression vector. Procedures for producing polynucleotide sequences encoding gp120 polypeptides and for manipulating them in vitro are well known to those of skill in the art. See Sambrook, 1989, and Ausubel, 2002, supra.

The polynucleotide sequences encoding an immunogenic gp120 polypeptide can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques that are well known to those of ordinary skill in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an immunogenic gp120 polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. See Gluzman Y, Ed., "Eukaryotic Viral Vectors" (Cold Spring Harbor Laboratory Press, Cold Spring Harbor, N.Y., US, 1982).

C. Antibodies

The gp120 variants and fragments thereof according to the present invention can also be used to generate antibodies capable of recognizing and neutralizing HIV when the virus or particles thereof are present in a biological fluid of a subject. Thus, in another aspect, the invention relates to an antibody which binds specifically to an immunogenic polypeptide according to the invention.

As it is used in the present invention, the term "antibody" relates to a monomeric or multimeric protein which comprises at least one polypeptide having the capacity for binding to a determined antigen and comprising all or part of the light or heavy chain variable region of an immunoglobulin molecule. Antibodies of the invention include, but are not limited to, monoclonal antibodies, monospecific antibodies, polyclonal antibodies, multispecific antibodies, diabodies, triabodies, tetrabodies, human antibodies, humanized antibodies, camelized antibodies, chimeric antibodies, single chain antibodies, single domain antibodies, Fab fragments, F(ab') fragments, $F(')_2$ fragments, Fv fragments (i.e., the smallest functional module of an antibody), single chain Fvs (scFv), disulfide-stabilized Fvs (dsFv), Fd, $V_H$, $V_L$, $V_\alpha$, $V_\beta$, and anti-idiotypic (anti-Id) antibodies (e.g. anti-Id antibodies to antibodies of the invention), intrabodies, and epitope-binding fragments of any of the above. In some embodiments, the antibodies are monoclonal antibodies. In other embodiments, the antibodies are Fv fragments, including $V_H$ and $V_L$, regions.

These antibodies may be generated by conventional means utilizing the peptides of this invention. See Kieber-Emmons T, et al., WO1991004273. For example, polyclonal antibodies may be generated by conventionally stimulating the immune system of a selected animal with one or both of the above-identified peptides, or multivalent constructs, allowing the immune system to produce natural antibodies thereto, and collecting these antibodies from the animal's blood or other biological fluid. High titer polyclonal antibodies may be obtained by using the multivalent constructs described above as antigens. The resulting antibodies are capable of binding the selected HTV antigen as it appears in the biological fluids of an infected subject.

Additionally, the peptides of the present invention may also be used to generate antibodies that can be used as templates to generate anti-idiotype antibodies having the internal image of the neutralizing epitope structure contained in the peptide sequence. These antibodies, polyclonal or monoclonal, can then be used in vaccine formulations or in active immunotherapy. Accordingly, the present invention also includes monoclonal or polyclonal antibodies that carry the internal image of the peptides, as well as methods for generating these antibodies. See Kieber-Emmons, supra.

Where it is desirable to obtain and utilize monoclonal antibodies (MAb) for the compositions and the methods of this invention, hybridoma cell lines expressing desirable MAbs may be generated by using available tumor cell lines with well-known conventional techniques. See Köhler G, Milstein C, Nature 1975; 256(5517):495-497.

Recombinant antibodies may be generated using known techniques for their production. See Huse W, et al., Science 1989; 246:1275-1281. Desirable high-titer antibodies may also be generated by applying known recombinant techniques to the monoclonal or polyclonal antibodies developed to these antigens. See Amit R, et al., Science 1986; 233: 747-753, Queen C, et al., Proc. Natl. Acad. Sci. USA 1988; 86:10029-10033; Riechmann L, et al., Nature 1988; 332: 323-327, and Barbas C, et al., Proc. Natl. Acad. Sci. USA 1992; 89:4457-4461 and Winter P, GB 2188638.

D. Immunogenic Compositions Capable of Generating Neutralizing Antibodies

The gp120 variant polypeptides and nucleic acid molecules encoding the variant gp120 polypeptides disclosed herein can be used as immunogens or to produce immunogens to elicit an immune response (immunogenic compositions) against gp120 or a gp120 expressing virus to prevent, reduce or control, for example, HIV-1 infection or its related symptoms. Following administration of a therapeutically effective amount of the disclosed therapeutic compositions, the subject can be monitored for HIV-1 infection, symptoms associated with HIV-1 infection, or both. Thus, in another aspect, the invention relates to an immunogenic composition comprising a HIV-1 gp120 variant polypeptide or an immunogenic fragment thereof according to the invention, a polynucleotide encoding said polypeptide or an expression vector comprising said polynucleotide.

Suitable immunogenic fragments of gp120 suitable for use in the immunogenic compositions include peptides of relatively small in size, such as about 5 to 100 amino acids in size, for example about 5, about 6, about 7, about 8, about 9, about 10, about 15, about 20, about 25, about 30, about 40, about 50, about 60, about 70, about 80, about 90, or about 100. Thus, fragments (e.g. epitopes or other antigenic fragments) of a gp120 polypeptide, such as any of the gp120 polypeptides described herein or a fragment thereof can be used as an immunogens.

The term "immunogenic composition" refers to a composition that elicits an immune response which produces antibodies or cell-mediated immune responses against a specific immunogen. Injectable compositions can be prepared, for instance, as liquid solutions, suspensions, and emulsions. The term "antigenic composition" refers to a composition that can be recognized by a host immune system. For example, an antigenic composition contains epitopes that can be recognized by humoral (e.g. antibody) and/or cellular (e.g. T lymphocytes) components of a host immune system.

The term "vaccine" refers to an immunogenic composition for in vivo administration to a host, which may be a primate, particularly a human host, to confer protection against disease, particularly a viral disease.

The immunogenic compositions according to the invention are useful for the treatment or prevention of diseases caused by HIV infection. In a further aspect, the invention relates to a peptide, a nucleic acid, a vector, an immunogenic composition or a vaccine according to the invention for use in the treatment or prevention of a disease resulting from HIV-1 infection. Alternatively, the invention relates to the use of a peptide, a nucleic acid, a vector, an immunogenic composition or a vaccine according to the invention for the manufacture of a medicament for the treatment or prevention of a disease resulting from HIV-1 infection. Alternatively, the invention relates to a method for the treatment or prevention in a subject of a disease resulting from HIV-1 infection which comprises the administration to said subject of a peptide, nucleic acid, vector, or immunogenic composition or a vaccine according to the invention.

The term "treatment", as used anywhere herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein).

Thus, "treatment," "treating," and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or immune deficiency.

The terms "prevent," "preventing," and "prevention", as used herein, refer to a decrease in the occurrence of pathological cells in an animal. The prevention may be complete (e.g. the total absence of pathological cells in a subject). The prevention may also be partial, such that for example the occurrence of pathological cells in a subject is less than that which would have occurred without the present invention. Prevention also refers to reduced susceptibility to a clinical condition.

The immunogenic compositions according to the invention may further comprise a pharmaceutically acceptable carrier.

A "pharmaceutically acceptable carrier," "pharmaceutically acceptable diluent," or "pharmaceutically acceptable excipient", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed, and is compatible with other ingredients of the formulation. For example, the carrier for a formulation containing polypeptides would not normally include oxidizing agents and other compounds that are known to be deleterious to polypeptides. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation. Adjuvants could for example be selected from the group consisting of: AlK(SO4)2, AlNa(SO4)2, AlNH4 (SO4), silica, alum, Al(OH)3, Ca3 (PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2 percent squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in *Corynebacterium parvum, Bordetella pertussis*, and members of the genus *Brucella, Titermax*, ISCOMS, Quil A, ALUN, Lipid A derivatives, choleratoxin derivatives, HSP derivatives, LPS derivatives, synthetic peptide matrixes or GMDP, interleukin 1, interleukin 2, Montanide ISA-51 and QS-21, CpG oligonucleotide, poly I:C and GM-CSF. See Hunter R, U.S. Pat. No. 5,554,372, and Jager E, Knuth A, WO1997028816.

A variant gp120 polypeptide according to the invention can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence. See Pozsgay V, et al., PNAS 1999; 96:5194-5197, Lee S, et al., J. Immunol. 1976; 116:1711-1718 and Dintzis R, et al., PNAS 1976; 73:3671-3675. Useful carriers include polymeric carriers, which can be natural (e.g. polysaccharides, polypeptides or proteins from bacteria or viruses), semi-synthetic or synthetic materials containing one or more functional groups to which a reactant moiety can be attached. Bacterial products and viral proteins (e.g. hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (e.g. streptococcal or staphylococcal cell walls and lipopolysaccharide (LPS)).

The present invention further relates to preventing or reducing symptoms associated with HIV infection. These include symptoms associated with the minor symptomatic phase of HIV infection, including, for instance, shingles, skin rash and nail infection, mouth sores, recurrent nose and throat infection, and weight loss. In addition, further symptoms associated with the major symptomatic phase of HIV infection, include, for example, oral and vaginal thrush (Candida), persistent diarrhea, weight loss, persistent cough, reactivated tuberculosis, and recurrent herpes infections, such as cold sores (herpes simplex). Symptoms of full-blown AIDS which can be treated in accordance with the present invention, include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii pneumonia* (PCP), herpes zoster (or shingles), nervous system problems, such as pains, numbness or "pins and needles" in the hands and feet, neurological abnormalities, Kaposi's sarcoma, lymphoma, tuberculosis, and other opportunistic infections.

Beneficial effects of the peptides, nucleic acids and vectors of the invention include, for example, preventing or delaying initial infection of an individual exposed to HIV; reducing viral burden in an individual infected with HIV; prolonging the asymptomatic phase of HIV infection; maintaining low viral loads in HIV infected patients whose virus levels have been lowered via anti-retroviral therapy (ART); increasing levels of CD4 T cells or lessening the decrease in CD4 T cells, both HIV-1 specific and non-specific, in drug naive patients and in patients treated with ART, increasing overall health or quality of life in an individual with AIDS; and prolonging life expectancy of an individual with AIDS. A clinician can compare the effect of immunization with the patient's condition prior to treatment, or with the expected condition of an untreated patient, to determine whether the treatment is effective in inhibiting AIDS.

The immunogenic composition can be administered by any means known to one skilled in the art, such as by intramuscular, subcutaneous or intravenous injection, and oral, nasal, or anal administration. See Banga A, "Parenteral Controlled Delivery of Therapeutic Peptides and Proteins," in Therapeutic Peptides and Proteins (Technomic Publishing Co., Inc., Lancaster, Pa., US, 1995). To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. See Banga, 1995, supra. A particulate carrier based on a synthetic polymer has been shown to act as an adjuvant to enhance the immune response, in addition to providing a controlled release. Aluminum salts can also be used as adjuvants to produce an immune response.

Immunogenic compositions can be formulated in unit dosage form, suitable for individual administration of precise dosages. In pulse doses, a bolus administration of an immunogenic composition that includes a disclosed immunogen is provided, followed by a time-period wherein no disclosed immunogen is administered to the subject, followed by a second bolus administration. A therapeutically effective amount of an immunogenic composition can be administered in a single dose, or in multiple doses, for example daily, during a course of treatment. In specific, non-limiting examples, pulse doses of an immunogenic composition that include a disclosed immunogen are administered during the course of a day, during the course of a week, or during the course of a month.

Immunogenic compositions can be administered whenever the effect (such as decreased signs, symptom, or laboratory results of HIV-1 infection) is desired. Generally, the dose is sufficient to treat or ameliorate symptoms or signs of disease without producing unacceptable toxicity to the subject. Systemic or local administration can be utilized.

Amounts effective for therapeutic use can depend on the severity of the disease and the age, weight, general state of the patient, and other clinical factors. Thus, the final determination of the appropriate treatment regimen will be made by the attending clinician. Typically, dosages used in vitro can provide useful guidance in the amounts useful for in situ administration of the pharmaceutical composition, and animal models may be used to determine effective dosages for treatment of particular disorders. See Gilman R, et al., Eds., Goodman and Gilman's: The Pharmacological Basis of Therapeutics, 8th Ed. (Pergamon Press, New York, N.Y., US, 1990), and Gennaro A, Ed., Remington's Pharmaceutical Sciences, 18th Ed. (Mack Publishing Co., Easton, Pa., US, 1990). Typically, the dose range for a gp120 polypeptide is from about 0.1 μg/kg body weight to about 100 mg/kg body weight. Other suitable ranges include doses of from about 1 μg/kg to 10 mg/kg body weight. In one example, the dose is about 1.0 μg to about 50 mg, for example, 1 μg to 1 mg, such as 1 mg peptide per subject. The dosing schedule can vary from daily to as seldom as once a year, depending on clinical factors, such as the subject's sensitivity to the peptide and tempo of their disease. Therefore, a subject can receive a first dose of a disclosed therapeutic molecule, and then receive a second dose (or even more doses) at some later time(s), such as at least one day later, such as at least one week later.

The pharmaceutical compositions disclosed herein can be prepared and administered in dose units. Solid dose units include tablets, capsules, transdermal delivery systems, and suppositories. The administration of a therapeutic amount can be carried out both by single administration in the form of an individual dose unit or else several smaller dose units and also by multiple administrations of subdivided doses at specific intervals. Suitable single or divided doses include, but are not limited to about 0.01, 0.1, 0.5, 1, 3, 5, 10, 15, 30, or 50 μg protein/kg/day.

The nucleic acid constructs encoding antigenic gp120 polypeptides described herein are used, for example, in combination, as pharmaceutical compositions (medicaments) for use in therapeutic, for example, prophylactic regimens (such as vaccines) and administered to subjects (e.g. primate subjects, such as human subjects) to elicit an immune response against one or more clade or strain of HIV. For example, the compositions described herein can be administered to a human (or non-human) subject prior to infection with HIV to inhibit infection by or replication of the virus. Thus, the pharmaceutical compositions described above can be administered to a subject to elicit a protective immune response against HIV. To elicit an immune response, a therapeutically effective (e.g. immunologically effective) amount of the nucleic acid constructs are administered to a subject, such as a human (or non-human) subject.

Immunization by nucleic acid constructs is well known in the art and taught, for example. See Robinson H, et al., U.S. Pat. No. 5,643,578 (which describes methods of immunizing vertebrates by introducing DNA encoding a desired antigen to elicit a cell-mediated or a humoral response); Weiner D, et al., U.S. Pat. No. 5,593,972 and Weiner D, et al., U.S. Pat. No. 5,817,637 (which describe operably linking a nucleic acid sequence encoding an antigen to regulatory sequences enabling expression), and Urban R, et al., U.S. Pat. No. 5,880,103 (which describes several methods of delivery of nucleic acids encoding immunogenic peptides or other antigens to an organism). The methods include liposomal delivery of the nucleic acids (or of the synthetic peptides themselves), and immune-stimulating constructs, or ISCOMS® negatively charged cage-like structures of 30-40 nm in size formed spontaneously on mixing cholesterol and QUIL A® (saponin).

For administration of gp120 nucleic acid molecules, the nucleic acid can be delivered intracellularly, for example, by expression from an appropriate nucleic acid expression vector which is administered so that it becomes intracellular, such as by use of a retroviral vector, by direct injection, by use of microparticle bombardment (e.g. a gene gun; Biolistic, Dupont Corp, Delware, Del., US), coating with lipids, cell-surface receptors or transfecting agents, or by administering it in linkage to a homeobox-like peptide which is known to enter the nucleus. See Morgan J, et al., U.S. Pat. No. 4,980,286, and Joliot A, et al., Proc. Natl. Acad. Sci. USA 1991; 88:1864-1868. The present invention includes all forms of nucleic acid delivery, including synthetic oligos, naked DNA, plasmid and viral, integrated or not into the genome.

In another approach to using nucleic acids for immunization, an immunogenic gp120 polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in TB immunization protocols provide other potential vehicles for the peptides of the invention. See Paoletti E, et al., U.S. Pat. No. 4,722,848, and Stover C, et al., Nature 1991; 351:456-460.

In one example, a viral vector is utilized. These vectors include, but are not limited to, adenovirus, herpes virus, vaccinia, or an RNA virus such as a retrovirus. In one example, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding a gp120 polypeptide into the viral vector, along with another gene that encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those skilled in the art will know of, or can readily ascertain without undue experimentation, specific polynucleotide sequences which can be inserted into the retroviral genome or attached to a viral envelope to allow target specific delivery of the retroviral vector containing the polynucleotide encoding a gp120 polypeptide.

Suitable formulations for the nucleic acid constructs, include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the composition for use in the inventive method is formulated to protect the nucleic acid constructs from damage prior to administration. For example, the composition can be formulated to reduce loss of the adenoviral vectors on devices used to prepare, store, or administer the expression vector, such as glassware, syringes, or needles. The compositions can be formulated to decrease the light sensitivity and/or temperature sensitivity of the components. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof.

In therapeutic applications, a therapeutically effective amount of the composition is administered to a subject prior to or following exposure to or infection by HIV. When administered prior to exposure, the therapeutic application can be referred to as a prophylactic administration (such as in the form of a vaccine). Single or multiple administrations of the compositions are administered depending on the dosage and frequency as required and tolerated by the subject. In one embodiment, the dosage is administered once as a bolus, but in another embodiment can be applied periodically until a therapeutic result, such as a protective immune response, is achieved. Generally, the dose is sufficient to treat or ameliorate symptoms or signs of disease without producing unacceptable toxicity to the subject. Systemic or local administration can be utilized.

In the context of nucleic acid vaccines, naturally occurring or synthetic immunostimulatory compositions that bind to and stimulate receptors involved in innate immunity can be administered along with nucleic acid constructs encoding the gp120 polypeptides. For example, agents that stimulate certain Toll-like receptors (such as TLR7, TLR8 and TLR9) can be administered in combination with the nucleic acid constructs encoding gp120 polypeptides. In some embodiments, the nucleic acid construct is administered in combination with immunostimulatory CpG oligonucleotides.

Nucleic acid constructs encoding gp120 polypeptides can be introduced in vivo as naked DNA plasmids. DNA vectors can be introduced into the desired host cells by methods known in the art, including but not limited to transfection, electroporation (e.g. transcutaneous electroporation), microinjection, transduction, cell fusion, DEAE dextran, calcium phosphate precipitation, use of a gene gun, or use of a DNA vector transporter. See Wu C, et al., J. Biol. Chem. 1992; 267:963-967, Wu C and Wu G, Biol. Chem. 1988; 263: 14621-14624, and Williams R, et al., Proc. Natl. Acad. Sci. USA 1991; 88:2726-2730. Methods for formulating and administering naked DNA to mammalian muscle tissue are also known. See Felgner P, et al., U.S. Pat. No. 5,580,859, and U.S. Pat. No. 5,589,466. Other molecules are also useful for facilitating transfection of a nucleic acid in vivo, such as cationic oligopeptides, peptides derived from DNA binding proteins, or cationic polymers. See Bazile D, et al., WO1995021931, and Byk G, et al., WO1996025508.

Another well known method that can be used to introduce nucleic acid constructs encoding gp120 immunogens into host cells is particle bombardment (aka biolistic transformation). Biolistic transformation is commonly accomplished in one of several ways. One common method involves propelling inert or biologically active particles at cells. See Sanford J, et al., U.S. Pat. No. 4,945,050, U.S. Pat. No. 5,036,006, and U.S. Pat. No. 5,100,792.

Alternatively, the vector can be introduced in vivo by lipofection. The use of cationic lipids can promote encapsulation of negatively charged nucleic acids, and also promote fusion with negatively charged cell membranes. See Felgner P, Ringold G, Science 1989; 337:387-388. Particularly useful lipid compounds and compositions for transfer of nucleic acids have been described. See Felgner P, et al., U.S. Pat. No. 5,459,127, Behr J, et al., WO1995018863, and Byk G, WO1996017823.

As with the immunogenic polypeptide, the nucleic acid compositions may be administered in a single dose, or multiple doses separated by a time interval can be administered to elicit an immune response against HIV. For example, two doses, or three doses, or four doses, or five doses, or six doses or more can be administered to a subject over a period of several weeks, several months or even several years, to optimize the immune response.

It may be advantageous to administer the immunogenic compositions disclosed herein with other agents such as proteins, peptides, antibodies, and other anti-HIV agents. Examples of such anti-HIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir osamprenavir, ritonavir, saquinavir, tipranavir, and the like, and fusion protein inhibitors such as enfuvirtide and the like. In certain embodiments, immunonogenic compositions are administered concurrently with other anti-HIV therapeutic agents. In certain embodiments, the immunonogenic compositions are administered sequentially with other anti-HIV therapeutic agents, such as before or after the other agent. One of ordinary skill in the art would know that sequential administration can mean immediately following or after an appropriate period of time, such as hours days, weeks, months, or even years later.

E. Methods for the Detection of Anti-HIV Antibodies in a Biological Sample and Methods for the Detection of a Neutralizing Antibody Response The immunogens described in the present invention are suitable for the identification in a sample from patient of antibodies specific for said immunogens. Since the immunogens according to the present invention specifically bind neutralizing antibodies, the immunogens can be used for the detection of those patients which have developed neutralizing antibodies. Thus, the antibodies can aid to the identification of personalized therapies based on whether a patient shows neutralizing antibodies or not. Thus, in another aspect, the invention relates to a method for the detection in a sample of neutralizing antibodies specific towards a virus comprising:

(i) contacting said sample with a polypeptide according to the invention, and (ii) detecting the formation of an immune complex between said polypeptide.

The terms and expressions “neutralizing antibodies”, “virus”, “polypeptide” have been described in detail above.

In a preferred embodiment, the virus is HIV and the polypeptide is a gp120 variant polypeptide or an immunogenic fragment thereof as defined above. In a more preferred embodiment, the sample is from an HIV-1 infected patient or from an AIDS vaccine recipient.

Any of a wide variety of assay formats may be used in accordance with the methods of the present invention. Such formats may be heterogeneous or homogeneous, sequential or simultaneous, competitive or noncompetitive. See Peterson M, et al., U.S. Pat. No. 5,563,036, Cheng A, et al., U.S. Pat. No. 5,627,080, Lee J, et al., U.S. Pat. No. 5,633,141, Peterson M, et al., U.S. Pat. No. 5,679,525, Draetta G, et al., U.S. Pat. No. 5,691,147, Lucas F, et al., U.S. Pat. No. 5,698,411, Yan C, et al., U.S. Pat. No. 5,747,352, Davidson R, U.S. Pat. No. 5,811,526, Oh C, et al., U.S. Pat. No. 5,851,778 and Landrum E, et al., U.S. Pat. No. 5,976,822. Such assays can be formatted to be quantitative, to measure the concentration or amount of an anti-HIV antibody, or they may be formatted to be qualitative, to measure the presence or absence of an anti-HIV antibody. Additional descriptions of immunoassays that may be adapted for use in accordance with the principles of the present invention are available in the scientific literature. See Gnann J, et al., Methods Enzymol. 1989; 178:693-714, Dopel S, et al., Eur. J. Clin. Chem. Clin. Biochem. 1991; 29:331-337, Manocha M, et al., Immunol. Lett. 2003; 85(3):275-278), Brattegaard K, et al., AIDS 1995; 9(6):656-657, Beristain C, et al., J. Clin. Lab. Anal. 1995; 9:347-350, Modrow S, et al., J. Acquir. Immune Defic. Syndr. 1989; 2:141-148, Gueye-Ndiaye A, et al., AIDS 1993; 7:475-481, Sabatier J, et al., AIDS 1989; 3:215-220, Sommerfelt M, et al., Expert Opin. Biol. Ther. 2004; 4:349-361, Alcaro M, et al., Curr. Protein Pept. Sci. 2003; 4:285-290, Smith R, et al., Arch. Pathol. Lab. Med. 1990; 114:254-258, Petrov R, et al., Biomed. Sci. 1990; 1:239-244, Zolla-Pazner S, Nat. Rev. Immunol. 2004; 4:199-210, Baillou A, et al., J. Clin. Microbiol. 1991; 29:1387-1391, and McGaughey G, et al., Curr. HIV Res. 2004; 2:193-204.

Heterogeneous immunoassay techniques involve typically the use of a solid phase material to which the reaction product becomes bound, but may be adapted to involve the binding of non-immobilized antigens and antibodies (i.e. a solution-phase immunoassay). The reaction product is separated from excess sample, assay reagents, and other substances by removing the solid phase from the reaction mixture (e.g. by washing). One type of solid phase immunoassay that may be used in accordance with the present invention is a sandwich immunoassay. In the sandwich assay, the more analyte present in the sample, the greater the amount of label present on the solid phase. This type of assay format is generally preferred, especially for the visualization of low analyte concentrations, because the appearance of label on the solid phase is more readily detected.

In accordance with a preferred embodiment of the present invention, a peptide of the present invention that is specifically reactive with an anti-HIV antibody is bound to a solid support (i.e. immobilized) and incubated in contact with the biological sample being tested for the presence of an anti-HIV antibody. A blocking agent may be added to reduce non-specific binding.

As will be appreciated, the peptide may be incubated with the biological sample in an unbound state and then subsequently bound to the solid support (i.e. immobilized). The supports are then preferably extensively treated (e.g. by washing) to substantially remove non-HIV antibodies that may be present but that failed to bind to the bound peptide. In consequence of such treatment, an immune complex forms between the peptide and anti-HIV antibody.

A detectably labeled second antibody (capable of binding to the initial antibody (e.g. an anti-human IgG antibody)) is then preferably added and the support is incubated under conditions sufficient to permit the second antibody to bind to any anti-HIV antibody that may be present. The support is then preferably extensively treated (e.g. by washing) to substantially remove any unbound second antibody. If anti-HIV antibody is present in the test sample, then the two antibodies will form an immune complex with the immobilized peptide (i.e. a second antibody/anti-HIV antibody/immobilized peptide sandwich). In such an assay, the detection of second antibody bound to the support is indicative of anti-HIV antibody in the sample being tested. See Schuurs A, et al., U.S. Pat. No. 3,791,932 and U.S. Pat. No. 4,016,043, and Pankratz T, et al., U.S. Pat. No. 5,876,935. The second antibody may be a natural immunoglobulin isolated from nonhuman species (e.g. anti-human IgG murine antibody, anti-human IgG goat antibody, anti-human IgM goat antibody), or it can be produced recombinantly or synthetically. It may be an intact immunoglobulin, or an immunoglobulin fragment (e.g. FAb, $F[Ab]_2$). As desired, other binding molecules (capable of binding to anti-HIV antibodies) may be employed in concert with or in lieu of such second antibodies. For example, the anti-HIV antibodies can be biotinylated and the second antibody can be replaced with labeled avidin or streptavidin.

To eliminate the bound-free separation step and reduce the time and equipment needed for a chemical binding assay, a homogeneous assay format may alternatively be employed. In such assays, one component of the binding pair may still be immobilized; however, the presence of the second component of the binding pair is detected without a bound-free separation. Examples of homogeneous optical methods are the EMIT method (Syva, Sunnyvale, Calif., US), which operates through detection of fluorescence quenching; the laser nephelometry latex particle agglutination method of Behringwerke (Marburg, Del.), which operates by detecting changes in light scatter; the LPIA latex particle agglutination method (Mitsubishi Chemical Industries, Tokyo, JP); the TDX fluorescence depolarization method (Abbott Laboratories, Abbott Park, Ill., US); and the fluorescence energy transfer method (Cis Bio International, Paris, FR). Any of such assays may be adapted for use in accordance with the objectives of the present invention.

The binding assay of the present invention may be configured as a competitive assay. In a competitive assay, the more anti-HIV antibody present in the test sample, the lower the amount of label present on the solid phase.

In a manner similar to the sandwich assay, the competitive assay can be conducted by providing a defined amount of a labeled anti-HIV antibody and determining whether the fluid being tested contains anti-HIV antibody that would compete with the labeled antibody for binding to the support. In such a competitive assay, the amount of captured labeled antibody is inversely proportional to the amount of analyte present in the test sample. Several assays of this kind have been described in the art. See Smith D, et al., U.S. Pat. No. 4,401,764, Clagett J, et al., U.S. Pat. No. 4,746,631, Li C, et al., U.S. Pat. No. 4,661,444, Chieregatt E, et al., GB 2084317, Mochida E, et al., U.S. Pat. No. 4,185,084, Sadeh D, et al., U.S. Pat. No. 4,243,749, Lucas F, et al., U.S. Pat. No. 5,698,411, Landrum, supra, Leuvering J, U.S. Pat. No. 4,313,734, Gribnau T, et al., U.S. Pat. No. 4,373,932, and Baugher B, et al., U.S. Pat. No. 5,501,985. The use of enzymes (especially alkaline phosphatase, beta-galactosidase, horse radish peroxidase, or urease) as the detectable label (i.e. an enzyme immunoassay or EIA) is preferred.

The presence of enzymatic labels may be detected through the use of chromogenic substrates (including those that evolve or adsorb fluorescent, UV, visible light) in response to catalysis by the enzyme label. More preferably, chemical labels may be employed (e.g. colloidal gold, latex bead labels).

Detection of label can be accomplished using multiple detectors, multipass filters, gratings, or spectrally distinct fluors. See Ward D, et al., U.S. Pat. No. 5,759,781. It is particularly preferred to employ peroxidase as an enzyme label, especially in concert with the chromogenic substrate 3,3',5,5'-tetramethylbenzidine (TMB), OPD, or ABTS. In the case of labeling of the antibodies with peroxidase as enzyme, it is possible to use the periodate technique or a method reported in which the partners are linked with a heterobifunctional reagent. See Nakane P, et al., J. Histochem. Cytochem. 1974; 22:1084-1090. Any of a wide variety of solid supports may be employed in the immunoassays of the present invention. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, and glass, especially glass fibers. The support can take the form of spheres, rods, tubes, and microassay or microtiter plates. Sheet-like structures such as paper strips, small plates, and membranes are likewise suitable. The surface of the carriers can be permeable and impermeable for aqueous solutions.

Although the foregoing description pertains to assaying for the presence of anti-HIV antibodies in biological samples that are fluids (e.g. sera, blood, urine, saliva, pancreatic juice, cerebrospinal fluid, semen), it will be appreciated that any fluidic biological sample (e.g. tissue or biopsy extracts, extracts of feces, sputum) may likewise be employed in the assays of the present invention. Most preferably, the biological sample being assayed will be serum or plasma.

Since the immunogens according to the present invention are capable of inducing the production of broadly neutralizing antibodies, these immunogens can also be used for the detection of a neutralizing antibody response to a pathogen in a patient. Thus, in another aspect, the invention relates to a method for the detection of a neutralizing antibody response against a virus infection in a subject comprising detecting in said subject the presence of neutralizing antibodies using a method for detecting neutralizing antibodies according to the invention, wherein the presence of neutralizing antibodies in said subject with respect to a control subject are indicative of an of a neutralizing antibody response to said virus infection in said subject.

In a preferred embodiment, the virus is HIV and wherein the polypeptide is a gp120 variant polypeptide or a fragment thereof according to the invention. In a more preferred embodiment, the sample is from an HIV-1 infected patient or from an AIDS vaccine recipient.

General Procedures

1. Reagents

The following reagents were utilized:

(a) Plasmids. The pNL4.3 plasmid was obtained from the National Institutes of Health AIDS Research and Reference Reagent Program (NIH ARRRP, NIH, Bethesda, Md., US). The pcDNA 3.1 plasmid was obtained from Invitrogen (Carslbad, Calif., US).

(b) HIV-1 isolate. A clade B HIV-1 primary isolate, AC-10, was used (NeutNet consortium, Milan, IT).

(c) Cell lines. TZM-b1 cells ($CD4^+$ $CXCR4^+CCR5^-$) were obtained from the NIH repository (NIH, Bethesda, Md., US). The 293T and TZM-bl cells were maintained in Dulbecco modified Eagle medium (DMEM) containing 10% fetal calf serum, 20 mM L-glutamine, 100 U of penicillin/ml, and 100 μg of streptomycin/ml.

(d) Antibodies. Anti-Env-HIV-1 monoclonal antibodies (MAbs) with broadly neutralizing activity (epitope specificities indicated in parentheses) were used (NIH ARRRP, NIH, Bethesda, Ma., US; Polymun AG, Vienna, AT). These included: 4E10 (membrane-proximal external region; MPER), 2F5 (MPER), b12 (CD4 binding site), 2G12 (gp120 high-mannose glycans), and PG16 (gp120 viral spikes).

2. In Vitro Random Mutagenesis

Mutations were introduced into HIV-1 AC-10 env using a Genemorph II Random Mutagenesis kit (Stratagene, La Jolla, Calif., US). A library of chimeric HIV virions was generated by transferring the randomly mutated envelopes into pNL4-3 and pcDNA3.1 plasmids. The transfer was mediated by the introduction of restriction sites preserving the virus sequence and digestion with the enzymes XbaI and NotI (New England Biolabs, Ipswich, Mass., US).

3. Cloning and Library Production

PCR products were cloned into the vectors pNL4.3 and pcDNA3.1 using the Rapid DNA Ligation Kit (Roche Applied Science, Indianapolis, Ind.) according to the manufacturer's specifications. The recombinant vectors of pNL4.3 and pcDNA3.1 were introduced into MAX Efficiency® Stbl2™ Competent Cells and MAX Efficiency® DH5α™ Competent Cells (Invitrogen, Carslbad, Calif., US), respectively, and amplified overnight (ON) at 30° C.

with agitation in a volume of 3 mL. Several transformations were performed simultaneously to avoid the loss of variability and mixed together in the upscaling of amplification (250 mL, 30° C., ON with agitation). After incubation, 20 μL were plated and the plasmid DNA purified using a PureYield™ Plasmid Maxiprep System (Promega, Madison, Wis., US). Both products were further digested with XbaI and NotI to verify the presence of the env gene. If positive, clones were sequenced and/or used for transfection. Viruses were produced by transient co-transfection of 293T cells using the pNL4.3 constructs. Cell culture supernatants containing virions were collected at 2 days post-transfection and virions were concentrated using an Amicon® Ultra centrifugal filter unit. Virions were re-suspended in phosphate-buffered saline (PBS).

4. Virion Capture Assay

Microtiter wells were coated overnight at 4° C. with polyclonal anti-Fc (5 μg/mL in 100 μl of PBS). Wells were blocked with 3% bovine serum albumin (BSA) in PBS for 1 h at 37° C. 100 μl of virus (1000 ng/mL) originating from the library was added to the microtiter wells. 5 μL of the capture MAbs (100 ng/mL) was added to the correspondent wells and the plate was incubated at 37° C. with agitation (450 rpm). After 2-hour incubation, the wells were washed six times with PBS, and virus equivalents were quantified by p24 enzyme-linked immunosorbent assay (ELISA) or the RNA extracted with the High Pure Viral RNA Kit (Roche Applied Science, Indianapolis, Ind., US) according to the manufacturer's instructions.

5. Nested RT-PCR HIV-1 env RNA Amplification

The isolated HIV-1 env RNA was amplified by reverse transcriptase polymerase chain reaction (RT-PCR) using a RT-PCR Kit (The GeneAmp® Gold RNA PCR Reagent Kit; Applied Biosystems, Carlsbad, Calif., US) and an Expand High Fidelity PCR System (Roche Applied Science, Indianapolis, Ind.). An RNA template volume of 8 μL was used for the RT-PCR reaction and the RNA was transcribed reversely with the primer 102 (reverse) at 50° C. for 20 min. The env region was amplified with the primers 101 (forward) and 104 (reverse) from a 5 μL volume of cDNA followed by a nested PCR with the primers 179 (forward) and 180 (reverse) using a 2 μL volume of template. See Table 1. The conditions of both env PCR amplifications were: i) 1 cycle of 94° C. for 2 min, ii) 35 cycles of 94° C. for 2 min, 55° C. for 1 min and 72° C. for 3 min, iii) 1 cycle of 72° C. for 7 min and iv) stop at 4° C. The resulting amplicon (2583 bp) was electrophoresed along with a 1 Kb molecular weight marker in 1.0% agarose gel stained with SYBR® Safe DNA gel stain.

6. Cloning and Sequencing of env Gene

The PCR products of the previous step were cloned into the pNL4.3 and pcDNA3.1 vectors as described above. Stb12 and DH5α competent cells were transformed with these plasmids as illustrated previously. The plasmid DNA was purified using a QIAprep Spin Miniprep Kit (Qiagen, Valencia, Calif., US) and further digested with XbaI and NotI to verify the presence of the env gene. Env-positive clones were sequenced using BigDye® Terminator v3.1 and the primers 183 (forward), 185 (forward), 186 (forward), 190 (reverse), 192 (reverse) and 193 (reverse). See Table 1.

7. Sequence Analysis

The alignment of the nucleotide sequences was conducted by using the CLUSTAL W program (EMBL-EBI, http://www.ebi.ac.uk/FTP/, February 2011) and Contig Assembly Program (CAP) applications integrated into the BioEdit 7.0.9.0 version and then edited by hand. See Thompson J, et al., Nucl. Acids Res. 1994; 22(22):673-4680 and Huang X, Genomics 1992; 14(1):18-25.

TABLE 1

Primer sequences and gene location.

| Primer ID | Sequence | Genome location | SEQ ID NO: |
|---|---|---|---|
| 101 | TAGAGCCCTGGAAGCATCCAGGAAG | 5853-5877 | 5 |
| 102 | TTGCTACTTGTGATTGCTCCATGT | 8936-8913 | 6 |
| 104 | AGCTGGATCCGTCTCGAGATACTGCTCCCACCC | 8916-8882 | 7 |
| 179 | GTAGTACATGTAATGCAACC | 6050-6069 | 8 |
| 180 | AGCTCGTCTCATTCTTTCCC | 8865-8846 | 9 |
| 183 | CCAATTCCCATACATTATTGTGC | 6858-6880 | 10 |
| 185 | GGAGCAGCAGGAAGCACTATGGGC | 7794-7817 | 11 |
| 186 | GAGTTAGGCAGGGATACTCACC | 8344-8365 | 12 |
| 190 | GCCAGGACTCTTGCCTGGAGCTG | 7969-7947 | 13 |
| 192 | CTTGTATTGTTGTTGGGTC | 7135-7117 | 14 |
| 193 | CATGGCTTTAGGCTTTGATCCC | 6580-6559 | 15 |

The gene location is based on the HIV-1 HXB2 genome (GenBank accession number K03455). [1]Wei X, et al., Antimicrob. Agents Chemother. 2002; 46(6): 1896-1905.

8. Production of Recombinant Viruses

Clones expressing envelope glycoproteins 4E10-specific with relevant mutations (loss of potential glycosylation sites and changes in the architecture of V1/V2 loops) were amplified ON, in a volume of 250 mL at 30° C. with agitation. Plasmid DNA was purified using a PureYield™ Plasmid Maxiprep System (Promega, Madison, Wis., US) and used for transient co-transfection of 293T cells. The pseudovirus-containing supernatants were harvested two days after transfection. The p24 level was quantified by ELISA.

9. Binding Assays

The binding of MAbs (4E10, 2F5, 2G12, b12, and PG16) to intact virions was determined with the capture assay described previously. First, the virus was incubated with the BMAbs in solution in order to facilitate virus-BMAb binding. Then, the virus-BMAb complexes were captured by the Anti FCs antibodies previously immobilized in the plate. The immobilized virus-BMAb were lysed with 1% Triton-X in PBS. The p24 in the virus lysate was quantified by ELISA as described above. A ΔEnv pNL4.3 construct was used as a negative control. Increase in binding affinity was determined by comparison with the wild type AC-10 virus.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

The invention claimed is:

1. A polypeptide capable of eliciting neutralizing antibodies against a virus, wherein the polypeptide comprises a variant HIV-1 gp120 or an immunogenic fragment thereof, and further wherein the variant gp120 or the immunogenic fragment thereof is selected from the group consisting of a polypeptide which comprises at least one mutation at a position selected from the group consisting of positions 88, 131, 132, 138, 160, 191, 203, 225, 479, 507, 604 and 647 with respect to the numbering of SEQ ID NO:2, wherein the polypeptide or the immunogenic fragment thereof comprises a sequence selected from the group consisting of SEQ ID NOs:4, 17, 19-29, and 31.

2. The polypeptide or the immunogenic fragment according to claim 1, wherein the polypeptide or the immunogenic fragment thereof comprises a sequence consisting of SEQ ID NO:4.

3. The polypeptide of claim 1, wherein the at least one mutation is selected from the group consisting of N88D, C131Y, T132N, D138G, N160Y, N191D, N203S, A225V, M479I, R507W, G604E, and Y647N with respect to the numbering of SEQ ID NO:2.

4. The polypeptide of claim 1, wherein the polypeptide or the immunogenic fragment thereof comprises a sequence selected from the group consisting of SEQ ID NOs:4 and 31.

5. A method for treating a disease caused by HIV infection in a subject, the method comprising administering to said subject a polypeptide according to claim 1.

6. A method for detecting neutralizing antibodies specific for HIV-1 present in a sample, the method comprising:

a. contacting said sample with a polypeptide according to claim 1; and b. detecting an immune complex formed between said polypeptide and said neutralizing antibodies, wherein neutralizing antibodies specific for HIV-1 present in the sample are detected.

7. A method for detecting a neutralizing antibody response against an HIV-1 virus infection in a subject, the method comprising:

(a) contacting a sample from said subject with a polypeptide according to claim 1;

(b) detecting an immune complex formed between said polypeptide and said neutralizing antibodies in said sample, wherein formation of said immune complex in said sample is indicative of a neutralizing antibody response to an HIV-1 virus infection in said subject.

8. The method according to claim 6, wherein the polypeptide comprises C131Y, T132N, D138G and N160Y mutations with respect to the numbering of SEQ ID NO:2 or comprises N203S and G604E mutations with respect to the numbering of SEQ ID NO:2.

9. The method according to claim 6, wherein the sample is from an HIV-1 infected patient or wherein the sample is from an AIDS vaccine recipient.

* * * * *